United States Patent
Sleat et al.

(10) Patent No.: US 11,370,984 B2
(45) Date of Patent: Jun. 28, 2022

(54) OIL TAGGING

(71) Applicant: FORECAST TECHNOLOGY LIMITED, Oxfordshire (GB)

(72) Inventors: Robert Sleat, Cardiff (GB); John Edward Minton, Cardiff (GB)

(73) Assignee: FORECAST TECHNOLOGY LIMITED, Oxfordshire (GB)

(*) Notice: Subject to any disclaimer, the term of this patent is extended or adjusted under 35 U.S.C. 154(b) by 429 days.

(21) Appl. No.: 16/481,798

(22) PCT Filed: Jan. 31, 2018

(86) PCT No.: PCT/GB2018/050284
§ 371 (c)(1),
(2) Date: Jul. 29, 2019

(87) PCT Pub. No.: WO2018/142131
PCT Pub. Date: Aug. 9, 2018

(65) Prior Publication Data
US 2021/0292668 A1    Sep. 23, 2021

(30) Foreign Application Priority Data

Jan. 31, 2017 (GB) .................... 1701574

(51) Int. Cl.
*C10L 1/00* (2006.01)
(52) U.S. Cl.
CPC .......... *C10L 1/003* (2013.01); *C10L 2230/16* (2013.01); *C10L 2270/026* (2013.01)

(58) Field of Classification Search
CPC ............ C10L 1/003; C10L 2270/026; C10L 2230/16; G01N 33/18; G01N 21/643
See application file for complete search history.

(56) References Cited

U.S. PATENT DOCUMENTS 5,665,538 A     9/1997 Slater et al.

FOREIGN PATENT DOCUMENTS

| EP | 338591 | * 10/1989 |
|---|---|---|
| WO | WO9014441 | * 11/1990 |
| WO | WO 91/17265 | 11/1991 |
| WO | WO 94/04918 | 3/1994 |
| WO | WO9942613 | * 8/1999 |
| WO | WO 00/39330 | 7/2000 |
| WO | WO 2012/030196 | 3/2012 |
| WO | WO 2013/157275 | 10/2013 |
| WO | WO 2016/114808 | 7/2016 |
| WO | WO 2016/172137 | 10/2016 |

OTHER PUBLICATIONS

Shibata et al. Chem. Commun., 2013, 49, 5501-5503.

* cited by examiner

*Primary Examiner* — Cephia D Toomer
(74) *Attorney, Agent, or Firm* — Karl Bozicevic; Bozicevic, Field & Francis LLP

(57) ABSTRACT

The invention provides a composition which comprises an apolar medium and a tracer compound, which tracer compound comprises a hydrophobic group and an oligonucleotide. Various uses of the tracer compound are also described.

17 Claims, 2 Drawing Sheets

Specification includes a Sequence Listing.

5' Modified Oligos

Zea02-C12-Amino

Zea02-Stearyl

Zea02-Palmitate

Zea02-Cholesterol-TEG

SEQUENCE LISTING

<160> NUMBER OF SEQ ID NOS: 4

<210> SEQ ID NO 1
<211> LENGTH: 60
<212> TYPE: DNA
<213> ORGANISM: Artificial Sequence
<220> FEATURE:
<223> OTHER INFORMATION: Zea02 single-stranded oligonucleotide

<400> SEQUENCE: 1
ccccatcagc acaaagctac aaaggcctaa tgggcgcgat taaggtcaag gctcagtcca        60

<210> SEQ ID NO 2
<211> LENGTH: 21
<212> TYPE: DNA
<213> ORGANISM: Artificial Sequence
<220> FEATURE:
<223> OTHER INFORMATION: Forward primer

<400> SEQUENCE: 2
ccccatcagc acaaagctac a        21

<210> SEQ ID NO 3
<211> LENGTH: 23
<212> TYPE: DNA
<213> ORGANISM: Artificial Sequence
<220> FEATURE:
<223> OTHER INFORMATION: Reverse primer

<400> SEQUENCE: 3
tggactgagc cttgacctta atc        23

<210> SEQ ID NO 4
<211> LENGTH: 14
<212> TYPE: DNA
<213> ORGANISM: Artificial Sequence
<220> FEATURE:
<223> OTHER INFORMATION: minor groove binder (MGB) probe

<400> SEQUENCE: 4
aggcctaatg ggcg        14

OIL TAGGING

FIELD OF THE INVENTION

The invention relates to the use of a tracer compound to label an apolar medium, for instance an oil or fuel present on a ship. The tracer compound is retained within the apolar medium, enabling it to be identified subsequently. The apolar medium may for instance have been discharged from a ship unlawfully into the water, and the tracer compound may be used to identify the apolar medium as having been on board the ship during a particular voyage.

BACKGROUND TO THE INVENTION

About 80% of world trade is carried by the international shipping industry in a world merchant fleet estimated at around 89,000 vessels (UNCTAD, 2015). The maritime industry may still be prone to commercial and political cycles but it is global in nature, mobile and growing, with seaborne trade predicted to double by 2030 (to between 19 and 24bn tonnes) in line with the forecast growth in international trade (Global Marine Trends 2030, Lloyds Register).

Such predicted increases in world seaborne trade and the increasing viability of shipping routes through the Arctic heighten the urgency for comprehensive international regulations that provide adequate environmental protection of our oceans and coastal waterways against the prospect of increased marine traffic.

The severe problems and ongoing threat that oil spills pose to marine ecosystems and the marine biodiversity that sustain them are well documented. It is estimated that each year a total of 100 million tonnes of heavy oils enter the world's oceans mostly as a result of deliberate rogue discharges by a minority of the world's fleet.

This form of intentional pollution is not permitted according to international conventions, but is quite frequent nevertheless (http://gcaptain.com/dsd-shipping-sentenced-to-pay-2-5-million-over-illegal-discharges/).

Known as operational oil spills, this deliberate type of discharge also encompasses the waste that some tankers dump overboard after cleaning their own tanks, which needs to be disposed of under controlled conditions. Despite the existence of legal and feasible ways to dispose of the oily waste water, operators, anxious to save time and money, prefer not to use expensive port cleaning facilities designed to handle the thousands of tonnes of crude sludge and slops and illegally discharge them at sea.

The risk of accidental oil spills has been addressed internationally through regulations implemented by the International Maritime Organisation (MARPOL 73/78) which limits the amount of oil which ships can legitimately discharge into the sea. Where discharge from bilge tanks is permitted, it is a requirement that an oil discharge monitoring and control system, together with oil filtering equipment (Oily Water Separator), be fitted to ensure that the oil content of any discharge does not exceed the maximum permitted under MARPOL (15 ppm). Any residue or sludge should then either be incinerated or discharged into reception tanks in port. Owners are required to demonstrate compliance with these regulations by the completion of log books, oil record books, incinerator logs and records of port discharges.

Despite these efforts, two problematic aspects remain. Firstly, the persistent difficulties of convicting polluting vessel operators. It seems that a coastal state has few possibilities to take legal action when illegal pollution is suspected. Secondly, it is a reasonable assumption that operators carefully choose where and when to clean tanks at sea, for example, spills during hours of darkness and in geographical areas where aerial oil spill surveillance is known to be lax, reduces the risk of getting caught.

SUMMARY OF THE INVENTION

The invention relates to a synthetic tracer which is designed to support the management of operational shipping activity to protect more effectively the marine environment. The synthetic tracer comprises a nucleic acid bonded to a hydrophobic moiety. The nucleic acid can be coded with a unique signature, so that it can effectively add a "fingerprint" to any on-board fluid that comprises an apolar medium which is not miscible with water, e.g. fuel oil hydrocarbons. The hydrophobic moiety ensures that the tracer is retained within the apolar medium if and when it comes into contact with water, so that the apolar medium remains "tagged" with the unique fingerprint even after contact with aqueous environments. This means that, for example, oil or fuel cargo could be tagged with the tracer's unique fingerprint, and the fingerprint would be retained in the oil or fuel in the event of a spill, because of the tracer's resistance to leaching into water. Likewise, the apolar oil or fuel components of aqueous slops containing these materials could also be tagged with a unique fingerprint, without the fingerprint leaching out of the apolar components and into the water. Applying the technology to oily waste water means that, should any such oil find its way into the ocean, if it were to be collected and sampled, the offending vessel could be held accountable and ultimately prosecuted.

In this way, the present invention will reinforce best practise towards safeguarding the marine environment. Safety and regulation are paramount in an industry which is expected to safeguard life and ensure safe operations at sea while protecting the marine environment. Maritime stakeholders are therefore particularly sensitive to the constantly evolving regulatory framework, driven by technological advancement and geopolitical events. Marine pollution is an issue affecting ship-owners, port authorities, shipbuilders and equipment suppliers with many looking for technologies to support their activities. The present invention will facilitate both government and IMO agendas in this field.

Accordingly, the present invention provides a composition which comprises an apolar medium and a tracer compound, which tracer compound comprises a hydrophobic group and an oligonucleotide. The tracer compound is typically a compound of formula (I)

wherein R is the hydrophobic group and Tag is the oligonucleotide. The tracer compound may however be a compound of formula (V)

wherein R is the hydrophobic group, Tag is the oligonucleotide, and $R^{II}$ is a second hydrophobic group which may be the same as or different from the first hydrophobic group.

The oligonucleotide is often referred to herein as an "identifiable oligonucleotide" on the basis that it can readily be identified by performing standard techniques on the tracer compound such as, for instance qPCR (quantitative polymerase chain reaction) followed by sequencing. Generally, the identifiable oligonucleotide of the tracer compound comprises a sequence of nucleotides which represents particular information about the material that is labelled or tagged with the tracer compound. It typically identifies the material that is labelled or tagged with the tracer compound (in the case of the present invention, the apolar material) as having a particular history or characteristic. This history or characteristic may for example be that the material has been on board a ship (or other kind of watercraft), for instance on a particular voyage.

The invention further provides a composition which comprises (i) an apolar medium, and (ii) a plurality of tracer compounds, wherein each tracer compound in the plurality comprises a hydrophobic group and an oligonucleotide, and wherein the oligonucleotide of each tracer compound in the plurality comprises a different unique sequence of nucleotides.

Typically, each of the different unique sequences of nucleotides will represent different information. For instance, each of the different unique sequences of nucleotides may provide a different piece of information about the apolar medium in the composition. These may be different pieces of information about the history of the apolar medium in terms of its whereabouts, e.g. that is has been on board a particular ship or other kind of watercraft, in a particular area on a particular watercraft, and/or on a particular voyage of a particular watercraft. The tracer compounds may also provide information about the mixing together of differently-tagged apolar media to form the apolar medium in the composition. The plurality of tracer compounds may allow detailed information to be built up about the history of a particular composition, for instance that is has been on board more than one particular voyage, that the apolar medium contains different components from different batches or for instance that the apolar medium is contaminated with one or more batches of apolar media from a different, previous voyage or from a different area in the watercraft.

The invention also provides a watercraft (for instance a ship or boat) having a composition on board, which composition comprises an apolar medium and a tracer compound, which tracer compound comprises a hydrophobic group and an identifiable oligonucleotide.

The invention further provides the use of a tracer compound for labelling an apolar medium, to enable identification of information about the apolar medium following discharge of the apolar medium from a watercraft into water, wherein the tracer compound comprises a hydrophobic group and an identifiable oligonucleotide.

The invention also provides the use of a tracer compound to identify information about an apolar medium following discharge of the apolar medium labelled with the tracer compound from a watercraft into water, wherein the tracer compound comprises a hydrophobic group and an identifiable oligonucleotide.

The tracer compound may for example be used to identify the apolar medium as having been on board the watercraft; on board the watercraft during a particular voyage; or present in a particular area, tank, container or bunker within the watercraft during a particular voyage. Indeed, the identifiable oligonucleotide of the tracer compound typically comprises a sequence of nucleotides which represents such information about the apolar medium.

The invention further provides a process for producing a composition which comprises an apolar medium and a tracer compound, which tracer compound comprises a hydrophobic group and an identifiable oligonucleotide, which process comprises treating a precursor composition comprising an apolar medium with said tracer compound.

In the process of the invention defined above, the precursor composition may further comprise water; or the process may further comprise treating the resulting composition with water. In this way, the process of the invention produces a composition which comprises the apolar medium and the tracer compound and which further comprises water. Generally, the apolar medium is immiscible with the water, and the composition comprises said tracer compound which is dissolved in the apolar medium.

The invention also provides a process for retrieving a tracer compound from a composition which comprises an apolar medium, the tracer compound and water, which tracer compound comprises a hydrophobic group and an identifiable oligonucleotide, which process comprises: (a) separating at least some of the apolar medium from water in the composition; and (b) extracting the tracer compound from the separated apolar medium.

The process for retrieving the tracer compound may further comprise: (c) analysing the identifiable oligonucleotide of the tracer compound to determine the identity of the oligonucleotide.

The invention also provides a method of labelling an apolar medium and subsequently identifying information about the apolar medium following discharge of the labelled apolar medium from a watercraft into water, the method comprising:

(i) treating a composition comprising an apolar medium with a tracer compound, wherein the tracer compound comprises a hydrophobic group and an identifiable oligonucleotide, and thereby producing a labelled apolar medium, wherein the labelled apolar medium comprises the apolar medium and the tracer compound, and wherein the labelled apolar medium is present on board a watercraft for a period of time;

(ii) after a discharge of said labelled apolar medium from the watercraft into the water, obtaining a sample comprising labelled apolar medium that was discharged;

(iii) retrieving the tracer compound from said sample;

(iv) analysing the identifiable oligonucleotide of the tracer compound to determine the identity of the oligonucleotide; and (v) using the identity of the oligonucleotide to identify information about the apolar medium.

The invention also provides a method of labelling an apolar medium to be carried on board a watercraft, which method comprises:

(i) treating a composition comprising an apolar medium with a tracer compound, wherein the tracer compound comprises a hydrophobic group and an identifiable oligonucleotide, and thereby producing a labelled apolar medium, wherein the labelled apolar medium comprises the apolar medium and the tracer compound.

The invention further provides a method of identifying information about an apolar medium after discharge of the apolar medium from a watercraft into the water, which method comprises:

(iii) retrieving a tracer compound from a sample comprising a labelled apolar medium that has been discharged from a watercraft into the water, wherein the labelled apolar medium comprises an apolar medium and a tracer compound, wherein the tracer compound comprises a hydrophobic group and an identifiable oligonucleotide; and (iv) analysing the identifiable oligonucleotide of the tracer compound to determine the identity of the oligonucleotide.

The method typically further comprises: (v) using the identity of the oligonucleotide to identify information about the apolar medium. By this method the apolar medium may be identified as apolar medium which was on board the watercraft; was on board the watercraft during a particular voyage; or was present in a particular area, tank, container or bunker within the watercraft during that voyage. The identifiable oligonucleotide of the tracer compound typically comprises a sequence of nucleotides which identifies the (labelled) apolar medium as having one or more of these characteristics.

DESCRIPTION OF THE SEQUENCE LISTING

Figure 1:
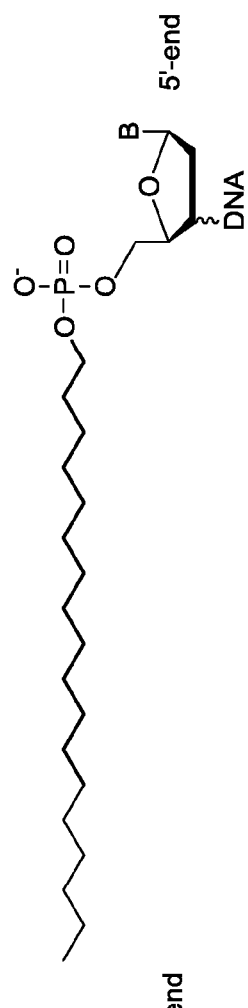
FIG. 1 shows the structures of four of the seven 5'-modified oligonucleotides that were evaluated as described in the Example hereinbelow, namely Zea02-C12-Amino, Zea02-Stearyl, Zea02-Palmitate, and Zea02-Cholesterol-TEG, where Zea02 is the oligonucleotide of SEQ ID NO: 1.
Figure 1:
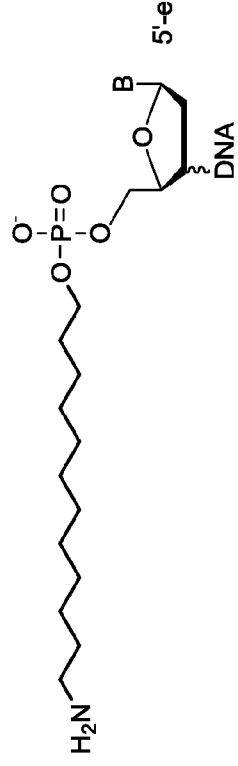
Figure 1:
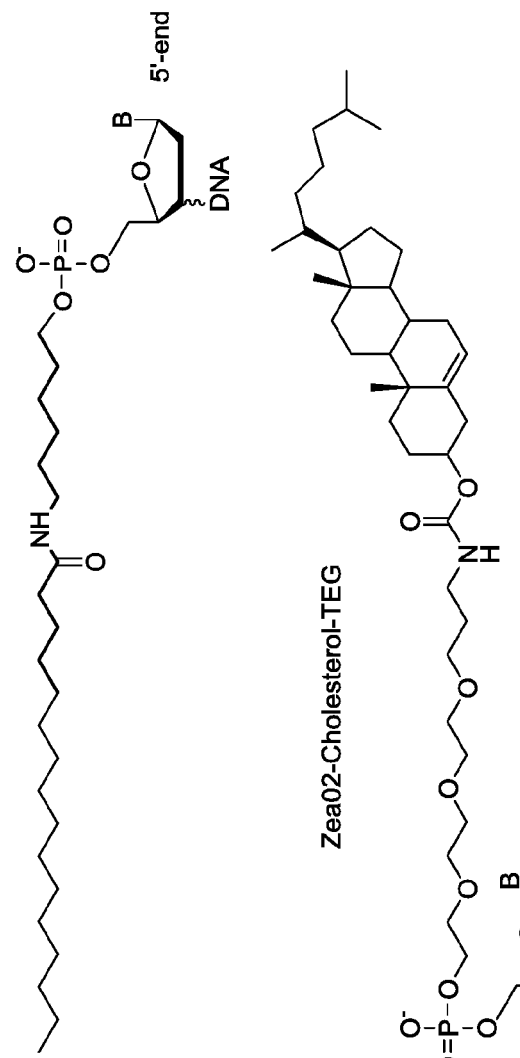
Figure 1:
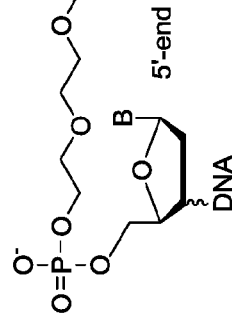

SEQ ID NO: 1 is the nucleotide sequence of the single stranded DNA molecule (oligonucleotide) employed in each of the 5'-modified oligonucleotides described in the Example hereinbelow. The oligonucleotide was given the code name Zea02.

SEQ ID NO: 2 is the nucleotide sequence of the forward primer used in the quantitative polymerase chain reaction employed to amplify and detect the 5'-modified oligonucleotides described in the Example hereinbelow.

SEQ ID NO: 3 is the nucleotide sequence of the reverse primer used in the quantitative polymerase chain reaction employed to amplify and detect the 5'-modified oligonucleotides described in the Example hereinbelow.

SEQ ID NO: 4 is the nucleotide sequence of the minor groove binder (MGB) probe used in the quantitative polymerase chain reaction employed to amplify and detect the 5'-modified oligonucleotides described in the Example hereinbelow.

DETAILED DESCRIPTION OF THE INVENTION

Chemical Compound and Substituent Definitions

The term "hydrocarbon", as used herein, takes its normal meaning. Thus, unless it is explicitly said to be a "substituted hydrocarbon", a hydrocarbon is a compound which consists only of carbon and hydrogen. For the avoidance of doubt, hydrocarbons include straight-chained and branched, saturated and unsaturated aliphatic hydrocarbon compounds, including alkanes, alkenes, and alkynes, as well as saturated and unsaturated cyclic aliphatic hydrocarbon compounds, including cycloalkanes, cycloalkenes and cycloalkynes. Hydrocarbons also include aromatic hydrocarbons, i.e. hydrocarbons comprising one or more aromatic rings. The aromatic rings may be monocyclic or polycyclic. Aliphatic hydrocarbons which are substituted with one or more aromatic hydrocarbons, and aromatic hydrocarbons which are substituted with one or more aliphatic hydrocarbons, are also of course encompassed by the term "hydrocarbon" (such compounds consisting only of carbon and hydrogen) as are straight-chained or branched aliphatic hydrocarbons that are substituted with one or more cyclic aliphatic hydrocarbons, and cyclic aliphatic hydrocarbons that are substituted with one or more straight-chained or branched aliphatic hydrocarbons.

A "substituted hydrocarbon" is a hydrocarbon as defined above which bears one or more non-hydrocarbon substituents. The one or more non-hydrocarbon substituents may be selected from cyano, amino, nitro, $C_{1-10}$ alkylamino, di($C_{1-10}$)alkylamino, arylamino, diarylamino, aryl($C_{1-10}$)alkylamino, amido, acylamido, hydroxy, oxo, halo, carboxy, ester, acyl, acyloxy, $C_{1-10}$ alkoxy, aryloxy, halo($C_{1-10}$)alkyl, sulfonic acid, thiol, $C_{1-10}$ alkylthio, arylthio, sulfonyl, phosphoric acid, phosphate ester, phosphonic acid and phosphonate ester. Typically, the one or more non-hydrocarbon substituents are selected from cyano, amino, nitro, amido, acylamido, hydroxy, oxo, halo, carboxy, ester, acyl, acyloxy, sulfonic acid, thiol, sulfonyl, phosphoric acid, phosphate ester, phosphonic acid and phosphonate ester When a hydrocarbon is substituted, it may for instance bear from 1 to 20 non-hydrocarbon substituents, for example 1, 2, 3 or 4 non-hydrocarbon substituents. For instance, a substituted hydrocarbon may have 1, 2 or 3 non-hydrocarbon substituents, or for example 1 or 2 non-hydrocarbon substituents.

A "$C_{n-m}$ hydrocarbon", where n and m are integers, is a hydrocarbon, as defined above, having from n to m carbon atoms. For instance, a $C_{1-150}$ hydrocarbon is a hydrocarbon as defined above which has from 1 to 150 carbon atoms, and a $C_{10-150}$ hydrocarbon is a hydrocarbon as defined above which has from 10 to 150 carbon atoms. A $C_{1-100}$ hydrocarbon is a hydrocarbon as defined above which has from 1 to 100 carbon atoms, and a $C_{10-100}$ hydrocarbon is a hydrocarbon as defined above which has from 10 to 100 carbon atoms. A $C_{1-50}$ hydrocarbon is a hydrocarbon as defined above which has from 1 to 50 carbon atoms, and a $C_{10-50}$ hydrocarbon is a hydrocarbon as defined above which has from 10 to 50 carbon atoms. A $C_{1-10}$ hydrocarbon is a hydrocarbon as defined above which has from 1 to 10 carbon atoms, and a $C_{1-4}$ hydrocarbon is a hydrocarbon as defined above which has from 1 to 4 carbon atoms.

The term "alkane", as used herein, refers to a linear or branched chain saturated hydrocarbon compound. A "$C_{n-m}$ alkane" refers to an alkane having from n to m carbon atoms. Thus, for instance, an alkane may be a $C_{1-20}$ alkane, i.e. an alkane having from 1 to 20 carbon atoms, or for instance a $C_{1-10}$ alkane, i.e. an alkane having from 1 to 10 carbon atoms. It may for instance be a $C_{1-8}$ alkane, a $C_{1-6}$ alkane, a $C_{1-5}$ alkane, or a $C_{1-4}$ alkane, or for instance a $C_{2-20}$ alkane, a $C_{2-10}$ alkane, a $C_{2-8}$ alkane, a $C_{2-6}$ alkane, a $C_{2-5}$ alkane, a $C_{2-4}$ alkane, or a $C_{2-3}$ alkane. It is often a $C_{1-4}$ alkane, $C_{1-3}$ alkane or $C_{2-3}$ alkane in the present invention. Examples of smaller alkanes, e.g. of a $C_{1-10}$ alkane, are for instance, methane, ethane, propane, butane, isobutane, pentane, isopentane, hexane, methylpentane, dimethylbutane, heptane, methylhexane, dimethylpentane, octane, methylheptane, dimethylhexane, trimethylpentane, nonane, decane. The term "n-alkane" as used herein, refers to a straight chain alkane. The term "i-alkane" as used herein, refers to a branched chain alkane. Alkanes such as dimethylbutane may be one or more of the possible isomers of this compound. Thus, dimethylbutane includes 2,3-dimethybutane and 2,2-dimethylbutane. This also applies for all hydrocarbon compounds referred to herein including cycloalkane, alkene, cycloalkene.

The term "cycloalkane", as used herein, refers to a saturated cyclic aliphatic hydrocarbon compound. A "$C_{n-m}$ cycloalkane" refers to a cycloalkane having from n to m carbon atoms. A cycloalkane may for instance be a $C_{3-20}$ cycloalkane, a $C_{3-10}$ cycloalkane, a $C_{3-8}$ cycloalkane, or a $C_{3-4}$ cycloalkane. Examples of a $C_{3-8}$ cycloalkane include cyclopropane, cyclobutane, cyclopentane, cyclohexane, methylcyclopentane, cycloheptane, methylcyclohexane, dimethylcyclopentane and cyclooctane. The terms "cycloalkane" and "naphthene" may be used interchangeably.

The term "alkene", as used herein, refers to a linear or branched chain hydrocarbon compound comprising one or more double bonds. A "$C_{n-m}$ alkene" refers to an alkene having from n to m carbon atoms. Thus, for instance, an alkene may be a $C_{2-20}$ alkene, i.e. an alkene having from 2 to 20 carbon atoms, or for instance a $C_{2-10}$ alkane, i.e. an alkane having from 2 to 10 carbon atoms. It may for instance be a $C_{2-8}$ alkane, a $C_{2-6}$ alkane, a $C_{2-5}$ alkane, a $C_{2-4}$ alkane, or a $C_{2-3}$ alkane. It is often a $C_{2-4}$ alkene or a $C_{2-3}$ alkene in the present invention. Examples of smaller alkenes, e.g. of $C_{2-12}$ alkenes are ethene (i.e. ethylene), propene (i.e. propylene), butene, pentene, methylbutene, hexene, methylpentene, dimethylbutene, heptene, methylhexene, dimethylpentene, octene, methylheptene, nonene, decene, undecene and dodecene. Alkenes typically comprise one or two double bonds. The terms "alkene" and "olefin" may be used interchangeably. The one or more double bonds may be at any position in the hydrocarbon chain. The alkenes may be cis- or trans-alkenes (or as defined using E- and Z-nomenclature). An alkene comprising a terminal double bond may be referred to as an "alk-1-ene" (e.g. hex-1-ene), a "terminal alkene" (or a "terminal olefin"), or an "alpha-alkene" (or an "alpha-olefin"). The term "alkene", as used herein also often includes cycloalkenes.

The term "cycloalkene", as used herein, refers to partially unsaturated cyclic hydrocarbon compound. A "$C_{n-m}$ cycloalkene" refers to a cycloalkene having from n to m carbon atoms. A cycloalkene may for instance be a $C_{3-20}$ cycloalkene a $C_{3-10}$ cycloalkene, a $C_{3-8}$ cycloalkene or a $C_{3-4}$ cycloalkene. Examples of a $C_{3-8}$ cycloalkene include cyclopropene, cyclobutene, cyclopentene, cyclohexene, cyclohexa-1,3-diene, methylcyclopentene, cycloheptene, methylcyclohexene, dimethylcyclopentene and cyclooctene. A cycloalkene may comprise one or two double bonds.

The term "aromatic compound", "aromatic hydrocarbon" or "aromatic hydrocarbon compound", as used herein, refers to a hydrocarbon compound comprising one or more aromatic rings. The aromatic rings may be monocyclic or polycyclic. Typically, an aromatic compound comprises a benzene ring. An aromatic compound may for instance be a $C_{6-14}$ aromatic compound, a $C_{6-12}$ aromatic compound or a $C_{6-10}$ aromatic compound. Examples of $C_{6-14}$ aromatic compounds are benzene, toluene, xylene, ethylbenzene, methylethylbenzene, diethylbenzene, naphthalene, methylnaphthalene, ethylnaphthalene and anthracene. The terms "aromatic compounds", "aromatics" and "arenes" may be used interchangeably.

The terms "hydrocarbyl group" and "hydrocarbyl", as used herein, refer to a radical of a hydrocarbon as defined above, obtainable by removing a hydrogen atom from the hydrocarbon.

A "$C_{n-m}$ hydrocarbyl group" or "$C_{n-m}$ hydrocarbyl" refers to a hydrocarbyl group having from n to m carbon atoms. For instance, "$C_{1-150}$ hydrocarbyl" refers to a hydrocarbyl group which has from 1 to 150 carbon atoms, and "$C_{5-60}$ hydrocarbyl" refers to a hydrocarbyl group which has from 5 to 60 carbon atoms.

A hydrocarbyl group is, unless otherwise specified an unsubstituted hydrocarbyl group. A hydrocarbyl group may however be substituted. The terms "substituted hydrocarbyl group" and "substituted hydrocarbyl", as used herein, refer to a hydrocarbyl group as defined above which bears one or more non-hydrocarbon substituents. The one or more non-hydrocarbon substituents may be selected from cyano, amino, nitro, $C_{1-10}$ alkylamino, di($C_{1-10}$)alkylamino, arylamino, diarylamino, aryl($C_{1-10}$)alkylamino, amido, acylamido, hydroxy, oxo, halo, carboxy, ester, acyl, acyloxy, $C_{1-10}$ alkoxy, aryloxy, halo($C_{1-10}$)alkyl, sulfonic acid, thiol, $C_{1-10}$ alkylthio, arylthio, sulfonyl, phosphoric acid, phosphate ester, phosphonic acid and phosphonate ester. Typically, the one or more non-hydrocarbon substituents are selected from cyano, amino, nitro, amido, acylamido, hydroxy, oxo, halo, carboxy, ester, acyl, acyloxy, sulfonic acid, thiol, sulfonyl, phosphoric acid, phosphate ester, phosphonic acid and phosphonate ester. When a hydrocarbyl group is substituted, it may for instance bear from 1 to 20 non-hydrocarbon substituents, for example 1, 2, 3 or 4 non-hydrocarbon substituents. For instance, a substituted hydrocarbyl group may have 1, 2 or 3 non-hydrocarbon substituents, or for example 1 or 2 non-hydrocarbon substituents.

However, when a hydrocarbyl group is halo-substituted, for instance fluoro-substituted, the hydrocarbyl group may for example bear from 1 to 20 halo substituents, for instance 1, 2, 3 or 4 halo substituents, or it may bear more than twenty halo substituents, depending on the number of carbon atoms in the hydrocarbyl group that can be substituted. The hydrocarbyl group may for instance be perhalo-substituted, i.e. all hydrogen atoms of the hydrocarbyl group may be replaced by halogen atoms. The hydrocarbyl group may for instance be perfluoro-substituted, i.e. perfluorinated, i.e. all hydrogen atoms of the group may be replaced by fluorine atoms. Accordingly, the term "substituted", as used herein, in the context of substituted hydrocarbyl groups (and substituted hydrocarbylene groups), encompasses the perhalo-substituted groups, in particular the perfluoro-substituted groups. Thus, for example, the term "substituted $C_{n-m}$ hydrocarbyl" as used herein encompasses $C_{n-m}$ perfluorohydrocarbyl and the term "substituted $C_{n-m}$ hydrocarbylene" as used herein encompasses $C_{n-m}$ perfluorohydrocarbylene.

The term "alkyl", as used herein, refers to a linear or branched chain saturated hydrocarbon radical. A "$C_{n-m}$ alkyl" refers to an alkyl having from n to m carbon atoms. Thus, an alkyl group may be a $C_{1-18}$ alkyl group, a $C_{1-14}$ alkyl group, a $C_{1-10}$ alkyl group, a $C_{1-6}$ alkyl group or a $C_{1-4}$ alkyl group. Examples of a $C_{1-10}$ alkyl group are methyl, ethyl, propyl, butyl, pentyl, hexyl, heptyl, octyl, nonyl or decyl. Examples of $C_{1-6}$ alkyl groups are methyl, ethyl, propyl, butyl, pentyl or hexyl. Examples of $C_{1-4}$ alkyl groups are methyl, ethyl, i-propyl, n-propyl, t-butyl, s-butyl or n-butyl. If the term "alkyl" is used without a prefix specifying the number of carbons anywhere herein, it has from 1 to 6 carbons.

The term "cycloalkyl", as used herein, refers to a saturated or partially unsaturated cyclic hydrocarbon radical. A "$C_{n-m}$ cycloalkyl" refers to a cycloalkyl having from n to m carbon atoms. Thus, a cycloalkyl group may be a $C_{3-10}$ cycloalkyl group, a $C_{3-8}$ cycloalkyl group or a $C_{3-6}$ cycloalkyl group. Examples of a $C_{3-8}$ cycloalkyl group include cyclopropyl, cyclobutyl, cyclopentyl, cyclohexyl, cyclohexenyl, cyclohex-1,3-dienyl, cycloheptyl and cyclooctyl. Examples of a $C_{3-6}$ cycloalkyl group include cyclopropyl, cyclobutyl, cyclopentyl, and cyclohexyl.

The term "alkenyl", as used herein, refers to a linear or branched chain hydrocarbon radical comprising one or more double bonds. A "$C_{n-m}$ alkenyl" refers to an alkenyl having from n to m carbon atoms. Thus, an alkenyl group may be a $C_{2-18}$ alkenyl group, a $C_{2-14}$ alkenyl group, a $C_{2-10}$ alkenyl group, a $C_{2-6}$ alkenyl group or a $C_{2-4}$ alkenyl group. Examples of a $C_{2-10}$ alkenyl group are ethenyl (vinyl), propenyl, butenyl, pentenyl, hexenyl, heptenyl, octenyl, nonenyl or decenyl. Examples of $C_{2-6}$ alkenyl groups are ethenyl, propenyl, butenyl, pentenyl or hexenyl. Examples of $C_{2-4}$ alkenyl groups are ethenyl, i-propenyl, n-propenyl, s-butenyl or n-butenyl. Alkenyl groups typically comprise one or two double bonds.

The term "alkynyl", as used herein, refers to a linear or branched chain hydrocarbon radical comprising one or more triple bonds. A "$C_{n-m}$ alkynyl" refers to an alkynyl having from n to m carbon atoms. Thus, an alkynyl group may be a $C_{2-18}$ alkynyl group, a $C_{2-14}$ alkynyl group, a $C_{2-10}$ alkynyl group, a $C_{2-6}$ alkynyl group or a $C_{2-4}$ alkynyl group. Examples of a $C_{2-10}$ alkynyl group are ethynyl, propynyl, butynyl, pentynyl, hexynyl, heptynyl, octynyl, nonynyl or decynyl. Examples of $C_{1-6}$ alkynyl groups are ethynyl, propynyl, butynyl, pentynyl or hexynyl. Alkynyl groups typically comprise one or two triple bonds.

The term "aryl", as used herein, refers to a monocyclic, bicyclic or polycyclic aromatic ring which contains from 6 to 14 carbon atoms, typically from 6 to 10 carbon atoms, in the ring portion. Examples include phenyl, naphthyl, indenyl and indanyl groups. The term "aryl group", as used herein, includes heteroaryl groups. The term "heteroaryl", as used herein, refers to monocyclic or bicyclic heteroaromatic rings which typically contains from six to ten atoms in the ring portion including one or more heteroatoms. A heteroaryl group is generally a 5- or 6-membered ring, containing at least one heteroatom selected from O, S, N, P, Se and Si. It may contain, for example, one, two or three heteroatoms. Examples of heteroaryl groups include pyridyl, pyrazinyl, pyrimidinyl, pyridazinyl, furanyl, thienyl, pyrazolidinyl, pyrrolyl, oxazolyl, oxadiazolyl, isoxazolyl, thiadiazolyl, thiazolyl, isothiazolyl, imidazolyl, pyrazolyl, quinolyl and isoquinolyl.

The terms "hydrocarbylene", "alkylene", "cycloalkylene", "alkenylene", "alkynylene", and "arylene", as used herein, refer to bivalent groups obtained by removing a hydrogen atom from a hydrocarbyl, alkyl, cycloalkyl, alkenyl, alkynyl, or aryl group, respectively. Such bidentate groups may be substituted or unsubstituted. An alkylene group may be a $C_{1-18}$ alkylene group, a $C_{1-14}$ alkylene group, a $C_{1-10}$ alkylene group, a $C_{1-6}$ alkylene group or a $C_{1-4}$ alkylene group. Examples of $C_{1-6}$ alkylene groups are methylene, ethylene, propylene, butylene, pentylene and hexylene. A cycloalkylene group may be a $C_{3-10}$ cycloalkylene group, a $C_{3-8}$ cycloalkylene group or a $C_{3-6}$ cycloalkylene group. Examples of $C_{3-6}$ cycloalkylene groups include cyclopentylene and cyclohexylene. An alkenylene group may be a $C_{2-18}$ alkenylene group, a $C_{2-14}$ alkenylene group, a $C_{2-10}$ alkenylene group, a $C_{2-6}$ alkenylene group or a $C_{2-4}$ alkenylene group. Examples of a $C_{2-4}$ alkenylene group include ethenylene (vinylene), propenylene and butenylene. An alkynylene group may be a $C_{2-18}$ alkynylene group, a $C_{2-14}$ alkynylene group, a $C_{2-10}$ alkynylene group, a $C_{2-6}$ alkynylene group or a $C_{2-4}$ alkynylene group. Examples of a $C_{2-4}$ alkynylene group include ethynylene and propynylene. Examples of arylene groups include phenylene and encompass heteroarylene groups such as, for instance, a diradical derived from thiophene, a diradical derived from chromane, and a diradical derived from chromanol. For alkylene, cycloalkylene, alkenylene, alkynylene, and arylene, these groups may be bonded to other groups at any two positions on the group. Thus, propylene includes —CH$_2$CH$_2$CH$_2$— and —CH$_2$CH(CH$_3$)—, and phenylene includes ortho-, meta- and para-phenylene.

The term "substituted", as used herein, in the context of substituted organic compounds and groups, refers to an organic compound or group, e.g. an alkane, an alkyl group, or an alkylene group, which bears one or more substituents selected from $C_{1-10}$ alkyl, aryl (as defined herein), cyano, amino, nitro, $C_{1-10}$ alkylamino, di($C_{1-10}$)alkylamino, arylamino, diarylamino, aryl($C_{1-10}$)alkylamino, amido, acylamido, hydroxy, oxo, halo, carboxy, ester, acyl, acyloxy, $C_{1-10}$ alkoxy, aryloxy, halo($C_{1-10}$)alkyl, sulfonic acid, thiol, $C_{1-10}$ alkylthio, arylthio, sulfonyl, phosphoric acid, phosphate ester, phosphonic acid and phosphonate ester. Typically, the one or more substituents are selected from cyano, amino, nitro, amido, acylamido, hydroxy, oxo, halo, carboxy, ester, acyl, acyloxy, sulfonic acid, thiol, sulfonyl, phosphoric acid, phosphate ester, phosphonic acid and phosphonate ester When a compound or group is substituted, it typically bears 1, 2, 3 or 4 substituents. For instance, a substituted compound or group may have 1, 2 or 3 substituents, or for example 1 or 2 substituents.

However, when a group is halo-substituted, for instance fluoro-substituted, the group may bear 1, 2, 3 or 4 halo substituents, or it may bear more than four halo substituents. In fact, the group may be perhalo-substituted, i.e. all hydrogen atoms of the group may be replaced by halogen atoms. The group may for instance be perfluoro-substituted, i.e. perfluorinated, i.e. all hydrogen atoms of the group may be replaced by fluorine atoms. Accordingly, the term "substituted", as used herein, in the context of substituted organic groups, for instance in the context of substituted hydrocarbyl groups, substituted alkyl groups, substituted cycloalkyl groups, substituted alkenyl groups, substituted alkynyl groups, substituted aryl groups, substituted hydrocarbylene groups, substituted alkylene groups, substituted cycloalkylene groups, substituted alkenylene groups, substituted alkynylene groups, and substituted arylene (including substituted heteroarylene) groups, encompasses the perhalo-substituted groups, in particular the perfluoro-substituted groups. Thus, for example, the term "substituted $C_{n-m}$ alkyl" as used herein encompasses $C_{n-m}$ perfluoroalkyl, the term "substituted $C_{n-m}$ alkylene" as used herein encompasses $C_{n-m}$ perfluoroalkylene, the term "substituted $C_{n-m}$ hydrocarbyl" as used herein encompasses $C_{n-m}$ perfluorohydrocarbyl and the term "substituted $C_{n-m}$ hydrocarbylene" as used herein encompasses $C_{n-m}$ perfluorohydrocarbylene, and so-on.

Apolar Medium

The apolar medium employed in the composition, uses, methods and processes of the invention is generally hydrophobic. It is generally immiscible with water.

The apolar medium employed in the composition, uses, methods and processes of the invention may comprise an unsubstituted or substituted hydrocarbon. The unsubstituted or substituted hydrocarbon may have a particular number of carbon atoms as defined further herein for substituted or unsubstituted hydrocarbons. Thus, the apolar medium may for instance comprise an unsubstituted or substituted $C_{10-150}$ hydrocarbon, or for instance an unsubstituted or substituted $C_{10-100}$ hydrocarbon, an unsubstituted or substituted $C_{10-50}$ hydrocarbon, an unsubstituted or substituted $C_{10-30}$ hydrocarbon, or an unsubstituted or substituted $C_{10-20}$ hydrocarbon.

The apolar medium often comprises a mixture of two or more different substituted or unsubstituted $C_{1-150}$ hydrocarbons. For instance, the apolar medium may comprise a mixture of two or more different substituted or unsubstituted $C_{5-150}$ hydrocarbons, for example a mixture of two or more different substituted or unsubstituted $C_{5-50}$ hydrocarbons, or for instance a mixture of two or more different substituted or unsubstituted $C_{5-30}$ hydrocarbons, or a mixture of two or more different substituted or unsubstituted $C_{5-20}$ hydrocarbons. The apolar medium may for instance comprise a mixture of two or more different unsubstituted or substituted $C_{10-150}$ hydrocarbons, or for instance a mixture of two or more different unsubstituted or substituted $C_{10-100}$ hydrocarbons, a mixture of two or more different unsubstituted or substituted $C_{10-50}$ hydrocarbons, a mixture of two or more different unsubstituted or substituted $C_{10-30}$ hydrocarbons, or a mixture of two or more different unsubstituted or substituted $C_{10-20}$ hydrocarbons.

The apolar medium employed in the composition, uses, methods and processes of the invention is typically a liquid. This means that the apolar medium is in the liquid state at standard ambient temperature and pressure (SATP), i.e. at a temperature of 298.15 K (25° C.) and at 100,000 Pa (1 bar, 14.5 psi, 0.9869 atm).

The apolar medium is typically a liquid comprising an unsubstituted or substituted hydrocarbon, wherein the unsubstituted or substituted hydrocarbon may be as further defined hereinbefore. The apolar medium is often a liquid comprising a mixture of two or more different unsubstituted or substituted hydrocarbons, wherein the mixture of two or more different unsubstituted or substituted hydrocarbons may be as further defined hereinbefore.

The apolar medium employed in the composition, uses, methods and processes of the invention often comprises a hydrocarbon (i.e. an unsubstituted hydrocarbon). The hydrocarbon may have a particular number of carbon atoms as defined further herein for hydrocarbons. The apolar medium may for instance comprise a $C_{10-150}$ hydrocarbon, or for instance a $C_{10-100}$ hydrocarbon, a $C_{10-50}$ hydrocarbon, a $C_{10-30}$ hydrocarbon, or a $C_{10-20}$ hydrocarbon.

The $C_{10-150}$ hydrocarbon, for instance the $C_{10-100}$, $C_{10-50}$, $C_{10-30}$, or $C_{10-20}$ hydrocarbon, may be an alkane, a cycloalkane, an alkene, a cycloalkene, or an aromatic compound. Thus, the hydrocarbon may be a $C_{10-50}$ alkane, or for instance a $C_{10-30}$ alkane or a $C_{10-20}$ alkane. Alternatively, the hydrocarbon may be a $C_{10-30}$ cycloalkane, or for example a $C_{10-20}$ cycloalkane. The hydrocarbon may for instance be a $C_{10-50}$ alkene, or for instance a $C_{10-30}$ alkene or a $C_{10-20}$ alkene. Alternatively, the hydrocarbon may be a $C_{10-30}$ cycloalkene, or for example a $C_{10-20}$ cycloalkene. The hydrocarbon may for instance be an aromatic hydrocarbon, for instance a $C_{10-16}$ aromatic hydrocarbon, for instance diethylbenzene, naphthalene, methylnaphthalene, ethylnaphthalene, anthracene, methylanthracene or ethylanthracene.

The apolar medium employed in the composition, uses, methods and processes of the invention often comprises a mixture of two or more different hydrocarbons (i.e. two or more different unsubstituted hydrocarbons). For instance, the apolar medium may comprise a mixture of two or more different $C_{1-150}$ hydrocarbons, such as a mixture of two or more different $C_{2-150}$ hydrocarbons, or for instance a mixture of two or more different $C_{5-150}$ hydrocarbons. For example, the apolar medium may comprise a mixture of two or more different $C_{5-50}$ hydrocarbons, or for instance a mixture of two or more different $C_{5-30}$ hydrocarbons, or a mixture of two or more different $C_{5-20}$ hydrocarbons. The apolar medium may for instance comprise a mixture of two or more different $C_{10-150}$ hydrocarbons, or for instance a mixture of two or more different $C_{10-100}$ hydrocarbons, a mixture of two or more different $C_{10-50}$ hydrocarbons, a mixture of two or more different $C_{10-30}$ hydrocarbons, or a mixture of two or more different $C_{10-20}$ hydrocarbons.

The mixture of two or more different hydrocarbons typically comprises two or more different hydrocarbons selected from alkanes, cycloalkanes, alkenes, cycloalkenes, and aromatic compounds. The mixture may for instance comprise two or more different hydrocarbons independently selected from $C_{5-50}$ alkanes (for instance from $C_{5-30}$ alkanes or from $C_{5-20}$ alkanes); $C_{4-30}$ cycloalkanes (for instance from $C_{5-20}$ cycloalkanes or from $C_{5-10}$ cycloalkanes); $C_{2-50}$ alkenes (for instance from $C_{5-30}$ alkenes or from $C_{5-20}$ alkenes); $C_{4-30}$ cycloalkenes (for instance from $C_{5-20}$ cycloalkenes or from $C_{5-10}$ cycloalkenes); $C_{6-16}$ aromatic hydrocarbons (for instance benzene, toluene, xylene, ethylbenzene, methylethylbenzene, diethylbenzene, naphthalene, methylnaphthalene, ethylnaphthalene, anthracene, methylanthracene or ethylanthracene). The mixture may for instance comprise two or more different hydrocarbons independently selected from $C_{5-30}$ alkanes, $C_{4-20}$ cycloalkanes, $C_{2-30}$ alkenes, $C_{4-20}$ cycloalkenes, and $C_{6-16}$ aromatic hydrocarbons. For example, the mixture may comprise two or more different hydrocarbons independently selected from $C_{5-20}$ alkanes, $C_{4-10}$ cycloalkanes, $C_{2-20}$ alkenes, $C_{4-10}$ cycloalkenes and $C_{6-16}$ aromatic hydrocarbons (for instance benzene, toluene, xylene, ethylbenzene, methylethylbenzene, diethylbenzene, naphthalene, methylnaphthalene, ethylnaphthalene, anthracene, methylanthracene or ethylanthracene).

The mixture of two or more different hydrocarbons may comprise gasoline range ($C_{5-12}$) hydrocarbons, or diesel range ($C_{5-24}$) hydrocarbons, or both. It may additionally or alternatively comprise one or more solid hydrocarbons, including paraffin waxes and hydrocarbon polymers, such as for instance, polyolefins, including for example polyethylene and polypropylene. The hydrocarbon polymers, may, for instance, be polyolefins, including for example polyethylene, polypropylene, polymethylpentene, polybutene-1, and including for instance polyolefin elastomers, such as, for example, polyisobutylene, ethylene propylene rubber, and ethylene propylene diene monomer (M-class) rubber. The hydrocarbon polymers may, for example, be hydrocarbon polymers which have a molecular weight of at least 1,800 Da.

Often, when the apolar medium comprises a mixture of two or more different hydrocarbons, at least one of those hydrocarbons is a $C_{10-150}$ hydrocarbon, for instance a $C_{10-100}$, $C_{10-50}$, $C_{10-30}$, or $C_{10-20}$ hydrocarbon. The $C_{10-150}$ hydrocarbon (or for instance the $C_{10-100}$, $C_{10-50}$, $C_{10-30}$, or $C_{10-20}$ hydrocarbon) may be as further defined hereinbefore.

As mentioned above, the apolar medium employed in the composition, uses, methods and processes of the invention is typically a liquid. The apolar medium is typically a liquid comprising a hydrocarbon, i.e. an unsubstituted hydrocarbon, wherein the (unsubstituted) hydrocarbon may be as further defined hereinbefore. The apolar medium is often a liquid comprising a mixture of two or more different hydrocarbons, i.e. two or more different unsubstituted hydrocarbons, wherein the mixture of the two or more different (unsubstituted) hydrocarbons may be as further defined hereinbefore.

The apolar medium may for instance be a petroleum product. Petroleum products are often transported as cargo on oil tankers.

The apolar medium may be a fuel, which may be fuel that is carried on board a watercraft as cargo or as the watercraft's fuel. It may for instance be gasoline (typically comprising a mixture of $C_{5-12}$ hydrocarbons), or diesel (typically comprising a mixture of $C_{8-24}$ hydrocarbons). Often, the apolar medium is, or comprises, fuel oil. The apolar medium may be, or may comprise, crude oil.

The apolar medium may for example comprise marine diesel. Marine diesel typically comprises a mixture of $C_{9-20}$ hydrocarbons. More typically, it comprises a mixture of $C_{10-20}$ hydrocarbons. Thus, in one embodiment the apolar medium comprises a mixture of two or more, for instance a mixture of five or more, or a mixture of ten or more, different $C_{10\text{-}20}$ hydrocarbons.

The apolar medium may comprise intermediate fuel oil. Intermediate fuel oil typically comprises a mixture of $C_{10\text{-}70}$ hydrocarbons, for instance a mixture of $C_{12\text{-}70}$ hydrocarbons. Thus, in one embodiment the apolar medium comprises a mixture of two or more, for instance a mixture of five or more, or a mixture of ten or more, different $C_{10\text{-}70}$ hydrocarbons. The apolar medium may for instance comprise a mixture of two or more, for instance a mixture of five or more, or a mixture of ten or more, different $C_{12\text{-}70}$ hydrocarbons.

The apolar medium may comprise heavy fuel oil. Heavy fuel oil typically comprises a mixture of $C_{20\text{-}70}$ hydrocarbons. Thus, in one embodiment the apolar medium comprises a mixture of two or more, for instance a mixture of five or more, or a mixture of ten or more, different $C_{20\text{-}70}$ hydrocarbons.

The apolar medium may comprise marine lubricant oil, for instance marine diesel engine lubricating oil.

The apolar medium may comprise crude oil.

Tracer Compound

The tracer compound comprises a hydrophobic group and an oligonucleotide. The oligonucleotide is often referred to herein as an "identifiable oligonucleotide" on the basis that the oligonucleotide can readily be identified by performing standard techniques on the tracer compound such as, for instance qPCR (quantitative polymerase chain reaction) followed by sequencing.

Generally, the hydrophobic group is covalently attached to the oligonucleotide. More specifically, the hydrophobic group is typically covalently bonded to one end of the oligonucleotide.

The hydrophobic group is usually attached to the 5' end of the oligonucleotide because it has thus far been found that attachment to the 5' end improves the ability to amplify the oligonucleotide using qPCR.

When the hydrophobic group (R) is attached to the 5' end of the oligonucleotide, it is typically covalently bonded to an oxygen atom of the phosphate group at the 5' end of the oligonucleotide, as follows:

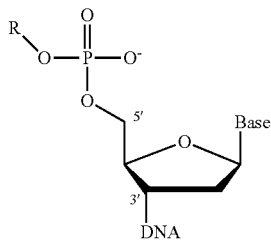

Figure 2:
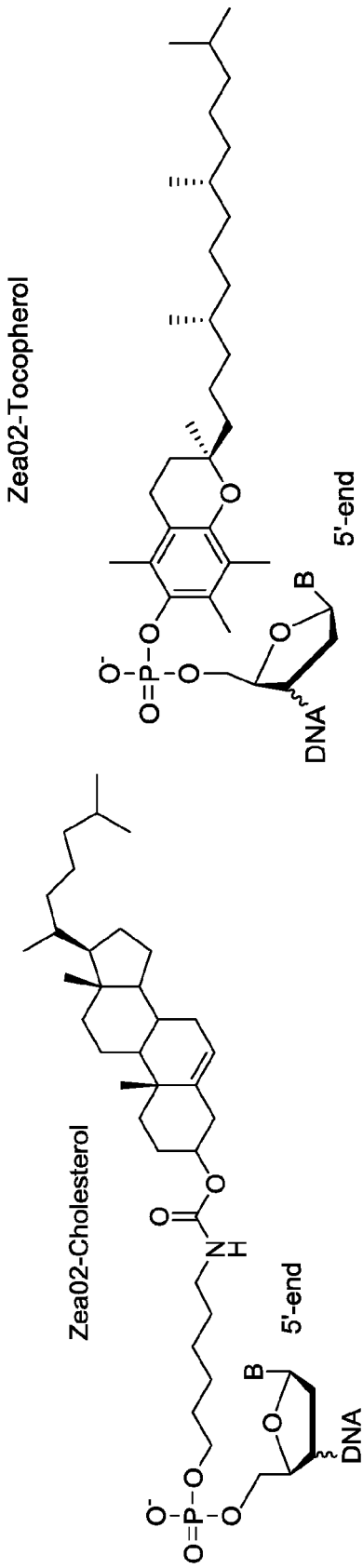
FIG. 2 shows the structures of the other three of the seven 5'-modified oligonucleotides that were evaluated as described in the Example hereinbelow, namely Zea02-Cholesterol, Zea02-Tocopherol and Zea02-Octyl-Tocopherol.
Figure 2:
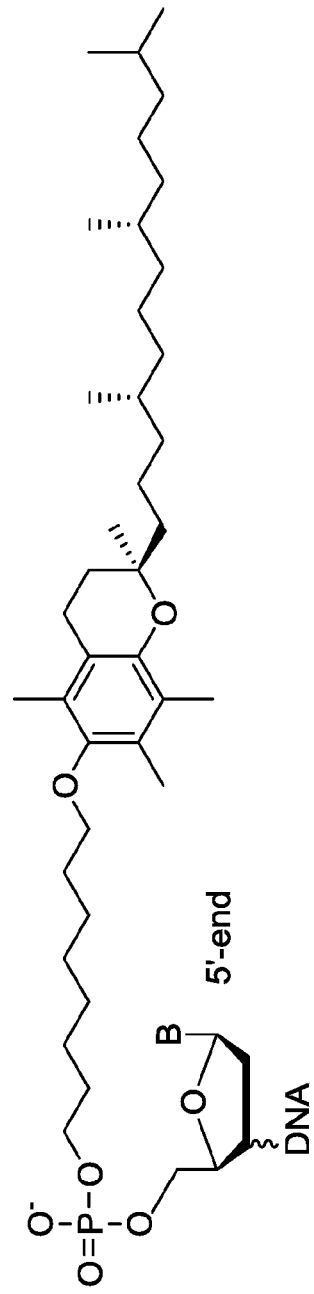

This is the phosphate group of the final nucleotide at the 5' end of the oligonucleotide. FIGS. 1 and 2 show how various different hydrophobic groups were bonded to the 5' end of an oligonucleotide (the oligonucleotide of SEQ ID NO: 1) in this way.

In another embodiment, however, the hydrophobic group is attached to the 3' end of the oligonucleotide. An advantage of this is that the hydrophobic group need not be attached after synthesis of the oligonucleotide, i.e. there is no need for post-synthesis attachment of a hydrophobic group. Instead, the hydrophobic modification may advantageously be carried out prior to synthesis of the oligonucleotide.

When the hydrophobic group is attached to the 3' end of the oligonucleotide, the hydrophobic group (R) may for instance be attached to the deoxyribose ring of the final nucleotide at the 3' end of the oligonucleotide, e.g. via a phosphate group bonded to the 3' carbon of that deoxyribose ring, as follows:

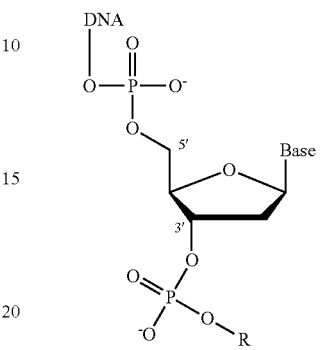

Thus, the hydrophobic group may be covalently bonded directly to an oxygen atom of a phosphate group at the 3' end of the oligonucleotide, wherein another oxygen atom of the same phosphate group (at the 3' end of the oligonucleotide) is covalently bonded directly to the 3' ring carbon of the sugar of the nucleotide at the 3' end of the oligonucleotide.

The tracer compound is typically a compound of formula (I):

$$\text{R-Tag} \tag{I}$$

wherein R is the hydrophobic group; and Tag is the identifiable oligonucleotide.

R is typically bonded to the 5' end of the identifiable oligonucleotide (i.e. to the 5' end of Tag). Usually, R is covalently bonded to the 5' end of Tag.

The bond (–) between R and Tag shown in formula (I) is covalent. It is generally a covalent single bond. It is usually a single bond between an atom (typically a carbon atom) of the hydrophobic group, R, and an oxygen atom of the phosphate group at the 5' end of the identifiable oligonucleotide. Thus, R may be covalently bonded to an oxygen atom of the phosphate group of the end nucleotide at the 5' end of Tag. Alternatively, the bond (–) between R and Tag shown in formula (I) may be a single bond between an atom (typically a carbon atom) of the hydrophobic group, R, and an oxygen atom of a phosphate group, which phosphate group is also covalently bonded (via another one of its oxygen atoms) to the end nucleotide at the 3' end of Tag. The phosphate group is usually covalently bonded to directly to the 3' carbon of the sugar ring of the nucleotide at the 3' end of the oligonucleotide.

The tracer compound may further comprise a second hydrophobic group, attached to the other end of the oligonucleotide. Thus, the "hydrophobic group" may be a "first hydrophobic group" and the tracer compound may further comprise a "second hydrophobic group". The second hydrophobic group may be the same as or different from the first hydrophobic group. The second hydrophobic group may be independently as defined anywhere herein for the first hydrophobic group.

Accordingly, the tracer compound may be a compound of formula (V)

$$\text{R-Tag-R}^{II} \tag{V}$$

wherein: R is the first hydrophobic group; R$^{II}$ is the second hydrophobic group; and Tag is the oligonucleotide. R in formula (V) may be as defined anywhere herein for R in the compound of formula (I). Similarly R$^{II}$ in formula (V) may be as defined anywhere herein for R in the compound of formula (I). R$^{II}$ in formula (V) may be the same as, or different from, R in formula (V).

Generally, in formula (V), one of R and R$^{II}$ is covalently bonded to the 5' end of Tag and the other one of R and R$^{II}$ is covalently bonded to the 3' end of Tag. For instance, one of R and R$^{II}$ may be covalently bonded to an oxygen atom of the phosphate group of the nucleotide at the 5' end of Tag and the other one of R and R$^{II}$ may be covalently bonded to an oxygen atom of a phosphate group which is attached to the nucleotide at the 3' end of Tag.

Hydrophobic Group

The or each hydrophobic group (denoted R in formula I, and R and R$^{II}$ in formula V) is any group which is hydrophobic so that, if and when the tracer compound were introduced into a liquid comprising water and an immiscible apolar medium as defined herein, the tracer compound would preferentially associate with (i.e. dissolve in) the apolar phase rather than the aqueous phase. It is possible for the hydrophobic group to comprise one or more substituents or moieties that on their own might not be considered hydrophobic. However, in that case, the hydrophobic group will comprise at least one other substituent or moiety (for instance a long hydrocarbon chain) which renders the group hydrophobic "overall". Indeed, in the present invention, it has been found that the hydrophobic group ensures that the tracer compound is retained within the apolar medium if and when it comes into contact with water, i.e. it is resistant to leaching out into the water. The apolar medium thereby remains "tagged" with the unique fingerprint of the identifiable oligonucleotide even after contact with aqueous environments.

The hydrophobic group, R, may be an unsubstituted or substituted hydrocarbyl group.

R may for instance be an unsubstituted or substituted $C_{1-200}$ hydrocarbyl group, or for instance an unsubstituted or substituted $C_{2-200}$ hydrocarbyl group. R may for example be an unsubstituted or substituted $C_{6-200}$ hydrocarbyl group, an unsubstituted or substituted $C_{4-200}$ hydrocarbyl group, or for instance an unsubstituted or substituted $C_{10-200}$ hydrocarbyl group, or an unsubstituted or substituted $C_{12-200}$ hydrocarbyl group.

R may for instance be an unsubstituted or substituted $C_{1-50}$ hydrocarbyl group, or for instance an unsubstituted or substituted $C_{2-50}$ hydrocarbyl group. R may for example be an unsubstituted or substituted $C_{6-50}$ hydrocarbyl group, or for instance an unsubstituted or substituted $C_{10-50}$ hydrocarbyl group, or an unsubstituted or substituted $C_{12-50}$ hydrocarbyl group.

R may for instance be an unsubstituted or substituted $C_{1-30}$ hydrocarbyl group, or for instance an unsubstituted or substituted $C_{2-30}$ hydrocarbyl group. R may for example be an unsubstituted or substituted $C_{6-30}$ hydrocarbyl group, or for instance an unsubstituted or substituted $C_{10-30}$ hydrocarbyl group, or an unsubstituted or substituted $C_{12-30}$ hydrocarbyl group.

The unsubstituted or substituted hydrocarbyl group as defined above may be an alkyl, cycloalkyl, alkenyl, alkynyl or aryl group, or it may comprise more than one of these group types. It may for instance consist of an alkyl, cycloalkyl, alkenyl, alkynyl or aryl group which is substituted with one or more other groups independently selected from alkyl, cycloalkyl, alkenyl, alkynyl and aryl groups.

Often, R is an unsubstituted or substituted $C_{1-200}$ alkyl group, for instance an unsubstituted or substituted $C_{2-200}$ alkyl group, for example an unsubstituted or substituted $C_{4-200}$ alkyl group, an unsubstituted or substituted $C_{6-200}$ alkyl group, an unsubstituted or substituted $C_{10-200}$ alkyl group, an unsubstituted or substituted $C_{12-200}$ alkyl group, or an unsubstituted or substituted $C_{16-200}$ alkyl group. R may for instance be an unsubstituted or substituted $C_{1-50}$ alkyl group, or for instance an unsubstituted or substituted $C_{6-50}$ alkyl group. R may for example be an unsubstituted or substituted $C_{10-50}$ alkyl group, or for instance an unsubstituted or substituted $C_{12-50}$ alkyl group, or an unsubstituted or substituted $C_{15-50}$ alkyl group. R may for instance be an unsubstituted or substituted $C_{1-30}$ alkyl group, or for instance an unsubstituted or substituted $C_{2-30}$ alkyl group. R may for example be an unsubstituted or substituted $C_{6-30}$ alkyl group, or for instance an unsubstituted or substituted $C_{10-30}$ alkyl group, or an unsubstituted or substituted $C_{12-30}$ alkyl group.

Alternatively, R may be an unsubstituted or substituted $C_{2-200}$ alkenyl or alkynyl group, for instance an unsubstituted or substituted $C_{4-200}$ alkenyl or alkynyl group, for example an unsubstituted or substituted $C_{10-200}$ alkenyl or alkynyl group, an unsubstituted or substituted $C_{12-200}$ alkenyl or alkynyl group, an unsubstituted or substituted $C_{16-200}$ alkenyl or alkynyl group, or an unsubstituted or substituted $C_{18-200}$ alkenyl or alkynyl group. R may for instance be an unsubstituted or substituted $C_{2-50}$ alkenyl or alkynyl group, or for instance an unsubstituted or substituted $C_{6-50}$ alkenyl or alkynyl group. R may for example be an unsubstituted or substituted $C_{10-50}$ alkenyl or alkynyl group, or for instance an unsubstituted or substituted $C_{12-50}$ alkenyl or alkynyl group, or an unsubstituted or substituted $C_{15-50}$ alkenyl or alkynyl group. R may for instance be an unsubstituted or substituted $C_{2-30}$ alkenyl or alkynyl group, or for instance an unsubstituted or substituted $C_{6-30}$ alkenyl or alkynyl group. R may for example be an unsubstituted or substituted $C_{10-30}$ alkenyl or alkynyl group, or for instance an unsubstituted or substituted $C_{12-30}$ alkenyl or alkynyl group, or an unsubstituted or substituted $C_{16-30}$ alkenyl or alkynyl group.

R may be an unsubstituted or substituted cycloalkyl group, for instance an unsubstituted or substituted $C_{4-30}$ cycloalkyl, an unsubstituted or substituted $C_{5-20}$ cycloalkyl or an unsubstituted or substituted $C_{5-10}$ cycloalkyl group. Alternatively, R may be an unsubstituted or substituted $C_{6-16}$ aryl group (for instance phenyl, tolyl, xylyl, ethylphenyl, methylethylphenyl, diethylphenyl, naphthyl, methylnaphthyl, ethylnaphthyl, anthracenyl, methylanthracenyl or ethylanthracenyl).

R may for instance be an unsubstituted or substituted $C_{4-200}$ alkyl group, an unsubstituted or substituted $C_{4-200}$ alkenyl group, an unsubstituted or substituted $C_{4-200}$ alkynyl group, an unsubstituted or substituted $C_{4-30}$ cycloalkyl group, or an unsubstituted or substituted $C_{6-16}$ aryl group.

R may for instance be an unsubstituted $C_{10-50}$ alkyl group or an amino-substituted $C_{10-50}$ alkyl group.

In some embodiments, R is an unsubstituted hydrocarbyl group as defined above. For instance, R may be an unsubstituted alkyl group as defined above. An example of an unsubstituted hydrocarbyl group is the following unsubstituted linear Cis alkyl group, which is a stearyl group:

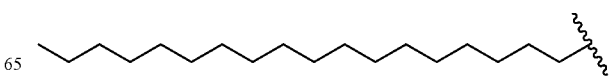

Alternatively, R may be a substituted hydrocarbyl group as defined above. For instance, R may be a substituted alkyl group as defined above. R may for instance be a substituted hydrocarbyl group as defined above which comprises one amino group substituent. An example of an amino-substituted hydrocarbyl group is the following amino-substituted alkyl group, which is referred to in the Example herein as "C12-amino":

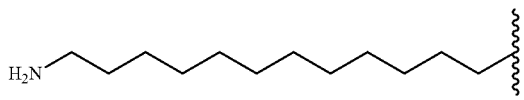 [SMILES: *CCCCCCCCCCCCN]

Advantageously, tracer compounds comprising a substituted hydrocarbyl group, and particularly an amino-substituted hydrocarbyl group, as the hydrophobic group showed a particularly high propensity for remaining with fuel oil hydrocarbons even when extensively and vigorously water washed.

R may be a substituted hydrocarbyl group as defined above which is perfluoro-substituted. R may for instance be a $C_{1-200}$ perfluorohydrocarbyl group, or for instance a $C_{2-200}$ perfluorohydrocarbyl group. R may for example be a $C_{4-200}$ perfluorohydrocarbyl group, a $C_{6-200}$ perfluorohydrocarbyl group, or for instance a $C_{10-200}$ perfluorohydrocarbyl group, or a $C_{12-200}$ perfluorohydrocarbyl group. R may for instance be a $C_{1-50}$ perfluorohydrocarbyl group, or for instance a $C_{2-50}$ perfluorohydrocarbyl group. R may for example be a $C_{6-50}$ perfluorohydrocarbyl group, or for instance a $C_{10-50}$ perfluorohydrocarbyl group, or a $C_{12-50}$ perfluorohydrocarbyl group. R may for instance be a $C_{1-30}$ perfluorohydrocarbyl group, or for instance a $C_{2-30}$ perfluorohydrocarbyl group. R may for example be a $C_{6-30}$ perfluorohydrocarbyl group, or for instance a $C_{10-30}$ perfluorohydrocarbyl group, or a $C_{12-30}$ perfluorohydrocarbyl group.

The perfluorohydrocarbyl group defined above may be a perfluoroalkyl, perfluorocycloalkyl, perfluoroalkenyl, perfluoroalkynyl or perfluoroaryl group, or it may comprise more than one of these group types. It may for instance consist of a perfluoroalkyl, perfluorocycloalkyl, perfluoroalkenyl, perfluoroalkynyl or perfluoroaryl group which is substituted with one or more other groups independently selected from perfluoroalkyl, perfluorocycloalkyl, perfluoroalkenyl, perfluoroalkynyl and perfluoroaryl groups.

Often, R is a $C_{1-200}$ perfluoroalkyl group, for instance a $C_{2-200}$ perfluoroalkyl group, for example a $C_{4-200}$ perfluoroalkyl group, a $C_{6-200}$ perfluoroalkyl group, a $C_{10-200}$ perfluoroalkyl group, a $C_{12-200}$ perfluoroalkyl group, or a $C_{16-200}$ perfluoroalkyl group. R may for instance be a $C_{1-50}$ perfluoroalkyl group, or for instance a $C_{6-50}$ perfluoroalkyl group. R may for example be a $C_{10-50}$ perfluoroalkyl group, or for instance a $C_{12-50}$ perfluoroalkyl group, or a Cis-so perfluoroalkyl group. R may for instance be a $C_{1-30}$ perfluoroalkyl group, or for instance a $C_2$-30 perfluoroalkyl group. R may for example be a $C_{6-30}$ perfluoroalkyl group, or for instance a $C_{10-30}$ perfluoroalkyl group, or a $C_{12-30}$ perfluoroalkyl group.

In some embodiments, the hydrophobic group, R, comprises an unsubstituted or substituted hydrocarbyl group, denoted $R^{HC}$, which is spaced apart from the identifiable oligonucleotide Tag by a linker group, denoted L.

Thus, in some embodiments, the hydrophobic group, R, is a group of formula (II)

$$R^{HC}\text{-L-} \tag{II}$$

wherein

L is bonded to Tag (typically to the 5' end of Tag) and is a linker group; and $R^{HC}$ is an unsubstituted or substituted hydrocarbyl group.

Often, L is covalently bonded directly to an oxygen atom of the phosphate group of the nucleotide at the 5' end of Tag. Alternatively, L may be covalently bonded directly to an oxygen atom of a phosphate group at the 3' end of Tag, wherein another oxygen atom of the phosphate group at the 3' end of Tag is covalently bonded directly to the 3' ring carbon of the nucleotide at the 3' end of Tag.

Typically, $R^{HC}$ is an unsubstituted or substituted $C_{1-200}$ hydrocarbyl group, or for instance an unsubstituted or substituted $C_{2-200}$ hydrocarbyl group. $R^{HC}$ may for example be an unsubstituted or substituted $C_{6-200}$ hydrocarbyl group, or for instance an unsubstituted or substituted $C_{10-200}$ hydrocarbyl group, or an unsubstituted or substituted $C_{12-200}$ hydrocarbyl group.

$R^{HC}$ may for instance be an unsubstituted or substituted $C_{1-50}$ hydrocarbyl group, or for instance an unsubstituted or substituted $C_{2-50}$ hydrocarbyl group. $R^{HC}$ may for example be an unsubstituted or substituted $C_{6-50}$ hydrocarbyl group, or for instance an unsubstituted or substituted $C_{10-50}$ hydrocarbyl group, or an unsubstituted or substituted $C_{12-50}$ hydrocarbyl group.

$R^{HC}$ may for instance be an unsubstituted or substituted $C_{1-30}$ hydrocarbyl group, or for instance an unsubstituted or substituted $C_{2-30}$ hydrocarbyl group. $R^{HC}$ may for example be an unsubstituted or substituted $C_{6-30}$ hydrocarbyl group, or for instance an unsubstituted or substituted $C_{10-30}$ hydrocarbyl group, or an unsubstituted or substituted $C_{12-30}$ hydrocarbyl group.

The unsubstituted or substituted hydrocarbyl group $R^{HC}$ as defined above may be an alkyl, cycloalkyl, alkenyl, alkynyl or aryl group, or it may comprise more than one of these group types. It may for instance consist of an alkyl, cycloalkyl, alkenyl, alkynyl or aryl group which is substituted with one or more other groups independently selected from alkyl, cycloalkyl, alkenyl, alkynyl and aryl groups.

Often, $R^{HC}$ is an unsubstituted or substituted $C_{1-200}$ alkyl group, for instance an unsubstituted or substituted $C_{2-200}$ alkyl group, an unsubstituted or substituted $C_{4-200}$ alkyl group, for example an unsubstituted or substituted $C_{6-200}$ alkyl group, an unsubstituted or substituted $C_{10-200}$ alkyl group, an unsubstituted or substituted $C_{12-200}$ alkyl group, or an unsubstituted or substituted $C_{16-200}$ alkyl group. $R^{HC}$ may for instance be an unsubstituted or substituted $C_{1-50}$ alkyl group, or for instance an unsubstituted or substituted $C_{6-50}$ alkyl group. $R^{HC}$ may for example be an unsubstituted or substituted $C_{10-50}$ alkyl group, or for instance an unsubstituted or substituted $C_{12-50}$ alkyl group, or an unsubstituted or substituted $C_{15-50}$ alkyl group. $R^{HC}$ may for instance be an unsubstituted or substituted $C_{1-30}$ alkyl group, or for instance an unsubstituted or substituted $C_{2-30}$ alkyl group. $R^{HC}$ may for example be an unsubstituted or substituted $C_{6-30}$ alkyl group, or for instance an unsubstituted or substituted $C_{10-30}$ alkyl group, or an unsubstituted or substituted $C_{12-30}$ alkyl group.

Alternatively, $R^{HC}$ may be an unsubstituted or substituted $C_{2-200}$ alkenyl or alkynyl group, for instance an unsubstituted or substituted $C_{4-200}$ alkenyl or alkynyl group, an unsubstituted or substituted $C_{6-200}$ alkenyl or alkynyl group, for example an unsubstituted or substituted $C_{10-200}$ alkenyl or alkynyl group, an unsubstituted or substituted $C_{12-200}$ alkenyl or alkynyl group, an unsubstituted or substituted $C_{16-200}$ alkenyl or alkynyl group, or an unsubstituted or substituted $C_{18-200}$ alkenyl or alkynyl group. R may for instance be an unsubstituted or substituted $C_{2-50}$ alkenyl or alkynyl group, or for instance an unsubstituted or substituted $C_{6-50}$ alkenyl or alkynyl group. $R^{HC}$ may for example be an unsubstituted or substituted $C_{10-50}$ alkenyl or alkynyl group, or for instance an unsubstituted or substituted $C_{12-50}$ alkenyl or alkynyl group, or an unsubstituted or substituted $C_{15-50}$ alkenyl or alkynyl group. $R^{HC}$ may for instance be an unsubstituted or substituted $C_{2-30}$ alkenyl or alkynyl group, or for instance an unsubstituted or substituted $C_{6-30}$ alkenyl or alkynyl group. $R^{HC}$ may for example be an unsubstituted or substituted $C_{10-30}$ alkenyl or alkynyl group, or for instance an unsubstituted or substituted $C_{12-30}$ alkenyl or alkynyl group, or an unsubstituted or substituted $C_{16-30}$ alkenyl or alkynyl group.

$R^{HC}$ may be an unsubstituted or substituted cycloalkyl group, for instance an unsubstituted or substituted $C_{4-30}$ cycloalkyl, an unsubstituted or substituted $C_{5-20}$ cycloalkyl or an unsubstituted or substituted $C_{5-10}$ cycloalkyl group. Alternatively, $R^{HC}$ may be an unsubstituted or substituted $C_{6-16}$ aryl group (for instance phenyl, tolyl, xylyl, ethylphenyl, methylethylphenyl, diethylphenyl, naphthyl, methylnaphthyl, ethylnaphthyl, anthracenyl, methylanthracenyl or ethylanthracenyl).

$R^{HC}$ may for instance be an unsubstituted or substituted $C_{4-200}$ alkyl group, an unsubstituted or substituted $C_{4-200}$ alkenyl group, an unsubstituted or substituted $C_{4-200}$ alkynyl group, an unsubstituted or substituted $C_{4-30}$ cycloalkyl group, or an unsubstituted or substituted $C_{6-16}$ aryl group.

In some embodiments, $R^{HC}$ is an unsubstituted hydrocarbyl group as defined above. $R^{HC}$ may for instance be an unsubstituted alkyl group as defined above.

Examples of unsubstituted hydrocarbyl groups $R^{HC}$ which may be employed, include the hydrocarbon polycyclic ring moiety of cholesterol, i.e.:

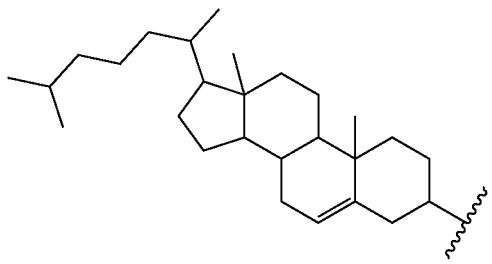 [SMILES: *C1CCC2(C)C(=CCC3C2CCC2(C)C(C(C)CCCC(C)C)CCC32)C1]

$R^{HC}$ may for instance be an unsubstituted $C_{6-50}$ alkyl group or the hydrocarbon polycyclic ring moiety of cholesterol, shown above.

Examples of unsubstituted alkyl groups $R^{HC}$ which may be employed, of course include both linear and branched unsubstituted alkyl groups, for example the following linear unsubstituted $C_{15}$ alkyl group:

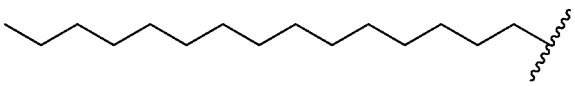 [SMILES: *CCCCCCCCCCCCCCC]

and the following branched unsubstituted $C_{16}$ alkyl group:

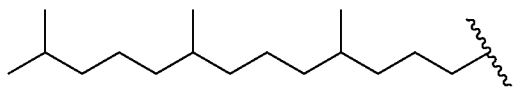 [SMILES: *CCCC(C)CCCC(C)CCCC(C)C]

$R^{HC}$ may also be a substituted hydrocarbyl group as defined above which is perfluoro-substituted. $R^{HC}$ may for instance be a $C_{1-200}$ perfluorohydrocarbyl group, or for instance a $C_{2-200}$ perfluorohydrocarbyl group. $R^{HC}$ may for example be a $C_{4-200}$ perfluorohydrocarbyl group, a $C_{6-200}$ perfluorohydrocarbyl group, or for instance a $C_{10-200}$ perfluorohydrocarbyl group, or a $C_{12-200}$ perfluorohydrocarbyl group. $R^{HC}$ may for instance be a $C_{1-50}$ perfluorohydrocarbyl group, or for instance a $C_{2-50}$ perfluorohydrocarbyl group. $R^{HC}$ may for example be a $C_{6-50}$ perfluorohydrocarbyl group, or for instance a $C_{10-50}$ perfluorohydrocarbyl group, or a $C_{12-50}$ perfluorohydrocarbyl group. $R^{HC}$ may for instance be a $C_{1-30}$ perfluorohydrocarbyl group, or for instance a $C_{2-30}$ perfluorohydrocarbyl group. $R^{HC}$ may for example be a $C_{6-30}$ perfluorohydrocarbyl group, or for instance a $C_{10-30}$ perfluorohydrocarbyl group, or a $C_{12-30}$ perfluorohydrocarbyl group.

The perfluorohydrocarbyl group $R^{HC}$ defined above may be a perfluoroalkyl, perfluorocycloalkyl, perfluoroalkenyl, perfluoroalkynyl or perfluoroaryl group, or it may comprise more than one of these group types. It may for instance consist of a perfluoroalkyl, perfluorocycloalkyl, perfluoroalkenyl, perfluoroalkynyl or perfluoroaryl group which is substituted with one or more other groups independently selected from perfluoroalkyl, perfluorocycloalkyl, perfluoroalkenyl, perfluoroalkynyl and perfluoroaryl groups.

Often, $R^{HC}$ is a $C_{1-200}$ perfluoroalkyl group, for instance a $C_{2-200}$ perfluoroalkyl group, a $C_{4-200}$ perfluoroalkyl group, for example a $C_{6-200}$ perfluoroalkyl group, a $C_{10-200}$ perfluoroalkyl group, a $C_{12-200}$ perfluoroalkyl group, or a $C_{16-200}$ perfluoroalkyl group. $R^{HC}$ may for instance be a $C_{1-50}$ perfluoroalkyl group, or for instance a $C_{6-50}$ perfluoroalkyl group. R may for example be a $C_{10-50}$ perfluoroalkyl group, or for instance a $C_{12-50}$ perfluoroalkyl group, or a $C_{15-50}$ perfluoroalkyl group. $R^{HC}$ may for instance be a $C_{1-30}$ perfluoroalkyl group, or for instance a $C_{2-30}$ perfluoroalkyl group. $R^{HC}$ may for example be a $C_{6-30}$ perfluoroalkyl group, or for instance a $C_{10-30}$ perfluoroalkyl group, or a $C_{12-30}$ perfluoroalkyl group.

Any suitable linker group may be employed as L.

The linker group, L, may for instance comprise a hydrocarbylene, alkylene, cycloalkylene, alkenylene, alkynylene or arylene (including heteroarylene) group as defined hereinbefore which may be unsubstituted or substituted (but is typically unsubstituted). The linker group may comprise one such group. Alternatively, it may comprise more than one such group, for instance two, three, four or five, hydrocarbylene, alkylene, cycloalkylene, alkenylene, alkynylene or arylene groups, as defined herein, bonded to one another, each of which may be unsubstituted or substituted (but is typically unsubstituted). The linker group may additionally or alternatively comprise one or more ether (—O—) linkages, one or more thio (—S—) linkages, one or more amino (—NR'—) linkages, one or more keto (—C(O)—) linkages, one or more ester (—OC(O)—) linkages, one or more amide (—C(O)—NR'—) linkages, or for instance one or more linkages of formula —O—C(O)—NR'—. Such linkages may for instance be present at one end of a hydrocarbylene, alkylene, cycloalkylene, alkenylene, alkynylene or arylene (including heteroarylene) group in the linker. R' in such linkages is generally H, unsubstituted $C_{1-4}$ alkyl or unsubstituted phenyl, and is usually H. The linker group may additionally or alternatively comprise a polyalkyleneglycol linkage of formula [—O-alk-]n wherein alk is $C_{2-4}$ alkylene (which $C_{2-4}$ alkylene may be linear or branched, and is typically unsubstituted) and n is from 2 to 200. Often, alk is ethylene, i.e. —CH$_2$—CH$_2$—. Typically, n is from 2 to 30, for instance from 2 to 20. More typically, alk is ethylene and n is from 2 to 10, for instance from 2 to 5.

Examples of linker groups, L, which are combinations of the above-listed groups include, but are by no means limited to linker groups of the following formulae:

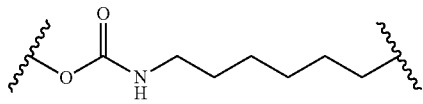 [SMILES: *CCCCCCNC(=O)O*]

(an example of a linker comprising an alkylene group bonded to a linkage of formula —O—C(O)—NH—);

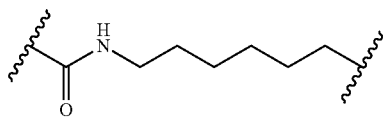 [SMILES: *CCCCCCNC(*)=O]

(an example of a linker comprising an alkylene group bonded to an amide linkage)

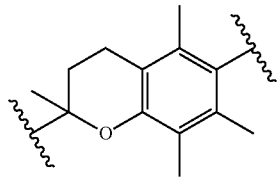 [SMILES: *c1c(C)c(C)c2c(c1C)CCC(*)(C)O2]

(an example of an arylene linker);

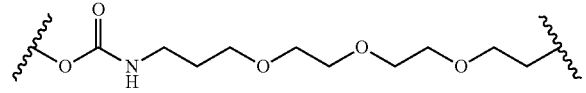 [SMILES: *CCOCCOCCOCCCNC(=O)O*]

(an example of a linker comprising a polyethyleneglycol group bonded to an alkylene group bonded to a linkage of formula —O—C(O)—NH—);

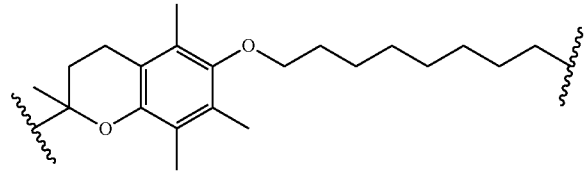 [SMILES: *CCCCCCCCOc1c(C)c(C)c2c(c1C)CCC(*)(C)O2]

(an example of a linker comprising an alkylene group bonded to a linkage of formula —O-bonded to an arylene group).

L is typically therefore unsubstituted or substituted $C_{1-200}$ hydrocarbylene, unsubstituted or substituted $C_{1-200}$ alkylene, unsubstituted or substituted $C_{4-30}$ cycloalkylene, unsubstituted or substituted $C_{2-200}$ alkenylene, unsubstituted or substituted $C_{2-200}$ alkynylene, unsubstituted or substituted $C_{6-16}$ arylene (including heteroarylene), —O—, —S—, —NR'—, —C(O)—, —OC(O)—, —C(O)—NR'—, —O—C(O)—NR'—, or [—O-alk-]$_n$, or is two or more of these groups (for instance from two to ten of these groups), which may be the same or different, bonded to one another, wherein alk is $C_{2-4}$ alkylene (which $C_{2-4}$ alkylene may be linear or branched, and is typically unsubstituted) and n is from 2 to 200.

L may for instance be unsubstituted or substituted $C_{1-200}$ hydrocarbylene, unsubstituted or substituted $C_{1-200}$ alkylene, unsubstituted or substituted $C_{4-30}$ cycloalkylene, unsubstituted or substituted $C_{2-200}$ alkenylene, unsubstituted or substituted $C_{2-200}$ alkynylene, unsubstituted or substituted $C_{6-16}$ arylene (including heteroarylene), —O—, —S—, —NR'—, —C(O)—NR'—, —O—C(O)—NR'—, or [—O-alk-]n, or is two or more of these groups (for instance from two to ten of these groups), which may be the same or different, bonded to one another, wherein alk is $C_{2-4}$ alkylene (which $C_{2-4}$ alkylene may be linear or branched, and is typically unsubstituted) and n is from 2 to 200.

When a substituted $C_{1-200}$ hydrocarbylene, substituted $C_{1-200}$ alkylene, substituted $C_{4-30}$ cycloalkylene, substituted $C_{2-200}$ alkenylene, substituted $C_{2-200}$ alkynylene or substituted $C_{6-16}$ arylene (including heteroarylene), is present in L, it may be a perfluoro-substituted group, i.e. it may be $C_{1-200}$ perfluorohydrocarbylene, $C_{1-200}$ perfluoroalkylene, $C_{4-30}$ perfluorocycloalkylene, $C_{2-200}$ perfluoroalkenylene, $C_{2-200}$ perfluoroalkynylene or $C_{6-16}$ perfluoroarylene (including perfluoroheteroarylene).

Often, alk is ethylene, i.e. —CH$_2$—CH$_2$—. Typically, n is from 2 to 30, for instance from 2 to 20. More typically, alk is ethylene and n is from 2 to 10, for instance from 2 to 5. R' is generally H, unsubstituted $C_{1-4}$ alkyl or unsubstituted phenyl, and is usually H.

L may for instance be unsubstituted or substituted $C_{1-60}$ hydrocarbylene, unsubstituted or substituted $C_{1-40}$ alkylene, unsubstituted or substituted $C_{4-30}$ cycloalkylene, unsubstituted or substituted $C_{2-60}$ alkenylene, unsubstituted or substituted $C_{6-16}$ arylene (including heteroarylene), —O—, —S—, —NR'—, —C(O)—, —OC(O)—, —C(O)—NR'—, —O—C(O)—NR'—, or [—O-alk-]n, or L may be two or more of these groups (for instance from two to ten of these groups), which may be the same or different, bonded to one another, wherein alk is $C_{2-4}$ alkylene (which $C_{2-4}$ alkylene may be linear or branched, and is typically unsubstituted) and n is from 2 to 200. Often, alk is ethylene, i.e. —CH$_2$—CH$_2$—. Typically, n is from 2 to 30, for instance from 2 to 20. More typically, alk is ethylene and n is from 2 to 10, for instance from 2 to 5. R' is generally H, unsubstituted $C_{1-4}$ alkyl or unsubstituted phenyl, and is usually H.

L may for instance be unsubstituted or substituted $C_{1-60}$ hydrocarbylene, unsubstituted or substituted $C_{1-40}$ alkylene, unsubstituted or substituted $C_{4-30}$ cycloalkylene, unsubstituted or substituted $C_{2-60}$ alkenylene, unsubstituted or substituted $C_{6-16}$ arylene (including heteroarylene), —O—, —S—, —NR'—, —C(O)—NR'—, —O—C(O)—NR'—, or [—O-alk-]n, or L may be two or more of these groups (for instance from two to ten of these groups), which may be the same or different, bonded to one another, wherein alk is $C_{2-4}$ alkylene (which $C_{2-4}$ alkylene may be linear or branched, and is typically unsubstituted) and n is from 2 to 200. Often, alk is ethylene, i.e. —CH$_2$—CH$_2$—. Typically, n is from 2 to 30, for instance from 2 to 20. More typically, alk is ethylene and n is from 2 to 10, for instance from 2 to 5. R' is generally H, unsubstituted $C_{1-4}$ alkyl or unsubstituted phenyl, and is usually H.

L may for instance be unsubstituted $C_{1-20}$ hydrocarbylene, unsubstituted $C_{1-20}$ alkylene, unsubstituted or substituted $C_{4-30}$ cycloalkylene, unsubstituted or substituted $C_{6-16}$ arylene (including heteroarylene), —O—, —S—, —NR'—, —C(O)—, —OC(O)—, —C(O)—NR'—, —O—C(O)—

NR'—, or [—O-alk-]$_n$, or two or more of any of these groups (for instance from two to five of these groups), which may be the same or different, bonded to one another, wherein alk is C$_{2-4}$ alkylene (which C$_{2-4}$ alkylene may be linear or branched, and is typically unsubstituted) and n is from 2 to 20. Often, alk is ethylene, i.e. —CH$_2$—CH$_2$—. Typically, n is from 2 to 10, for instance from 2 to 5. More typically, alk is ethylene and n is from 2 to 10, for instance from 2 to 5. R' is generally H, unsubstituted C$_{1-4}$ alkyl or unsubstituted phenyl, and is usually H.

L may for instance be unsubstituted C$_{1-20}$ hydrocarbylene, unsubstituted C$_{1-20}$ alkylene, unsubstituted or substituted C$_{4-30}$ cycloalkylene, unsubstituted or substituted C$_{6-16}$ arylene (including heteroarylene), —O—, —S—, —NR'—, —C(O)—NR'—, —O—C(O)—NR'—, or [—O-alk-]n, or two or more of any of these groups (for instance from two to five of these groups), which may be the same or different, bonded to one another, wherein alk is C$_{2-4}$ alkylene (which C$_{2-4}$ alkylene may be linear or branched, and is typically unsubstituted) and n is from 2 to 20. Often, alk is ethylene, i.e. —CH$_2$—CH$_2$—. Typically, n is from 2 to 10, for instance from 2 to 5. More typically, alk is ethylene and n is from 2 to 10, for instance from 2 to 5. R' is generally H, unsubstituted C$_{1-4}$ alkyl or unsubstituted phenyl, and is usually H.

Usually, the linker group does not contain a group of the following formula:

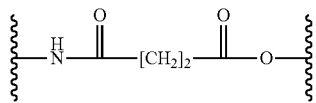

Often, the linker group does not contain a group of the following formula:

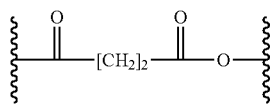

The linker group typically does not contain a group of the following formula:

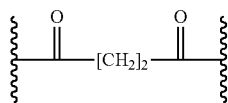

In some embodiments, the linker group, L, is a group of formula -L$^3$-L$^2$-L$^1$- wherein:

L$^1$ is bonded to Tag and is unsubstituted or substituted C$_{1-200}$ hydrocarbylene, unsubstituted or substituted C$_{6-16}$ arylene or heteroarylene, or [—O-alk-]$_n$, wherein alk is linear or branched unsubstituted C$_{2-4}$ alkylene and n is from 2 to 200;

L$^2$ is a single bond, unsubstituted or substituted C$_{1-200}$ hydrocarbylene, —O—, —N(R')—, —C(O)—, —C(O)—N(R')— or —O—C(O)—NR'—; and L$^3$ is a single bond, —O—C(O)—NR'—, unsubstituted or substituted C$_{6-16}$ arylene or heteroarylene, wherein R' is H, unsubstituted C$_{1-4}$ alkyl or unsubstituted phenyl.

Often, L$^1$ is covalently bonded directly to an oxygen atom of the phosphate group of the nucleotide at the 5' end of Tag. Alternatively, L$^1$ may be covalently bonded directly to an oxygen atom of a phosphate group at the 3' end of Tag, wherein another oxygen atom of the phosphate group at the 3' end of Tag is covalently bonded directly to the 3' ring carbon of the nucleotide at the 3' end of Tag.

Thus, the linker group, L, may be a group of formula -L$^3$-L$^2$-O— wherein:

L$^1$ is bonded to Tag and is unsubstituted or substituted C$_{1-50}$ hydrocarbylene, unsubstituted or substituted C$_{6-16}$ arylene or heteroarylene, or [—O-alk-]$_n$, wherein alk is linear or branched unsubstituted C$_{2-4}$ alkylene and n is from 2 to 50;

L$^2$ is a single bond, unsubstituted or substituted C$_{1-50}$ hydrocarbylene, —O—, —N(R')—, —C(O)—, —C(O)—N(R')— or —O—C(O)—NR'—; and L$^3$ is a single bond, —O—C(O)—NR'—, unsubstituted or substituted C$_{6-16}$ arylene or heteroarylene, wherein R' is H, unsubstituted C$_{1-4}$ alkyl or unsubstituted phenyl.

The linker group, L, may for instance be a group of formula -L$^3$-L$^2$-L$^1$- wherein:

L$^1$ is bonded to Tag and is unsubstituted or substituted C$_{1-20}$ alkylene, unsubstituted or substituted C$_{6-16}$ arylene or heteroarylene, or [—O-alk-]$_n$, wherein alk is —CH$_2$CH$_2$— and n is from 2 to 50, for instance from 2 to 10, or from 2 to 6;

L$^2$ is a single bond, unsubstituted or substituted C$_{1-20}$ alkylene, —O—, —N(R')—, —C(O)—, —C(O)—N(R')— or —O—C(O)—NR'—, and L$^3$ is a single bond, —O—C(O)—NR'—, unsubstituted or substituted C$_{6-16}$ arylene or heteroarylene, wherein R' is H, unsubstituted C$_{1-4}$ alkyl or unsubstituted phenyl.

R' is typically H.

The hydrophobic group, R, in the tracer compound may for instance be a group of any one of the following formulae:

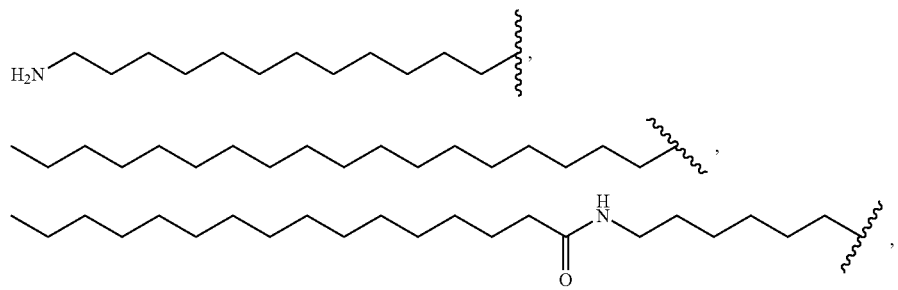

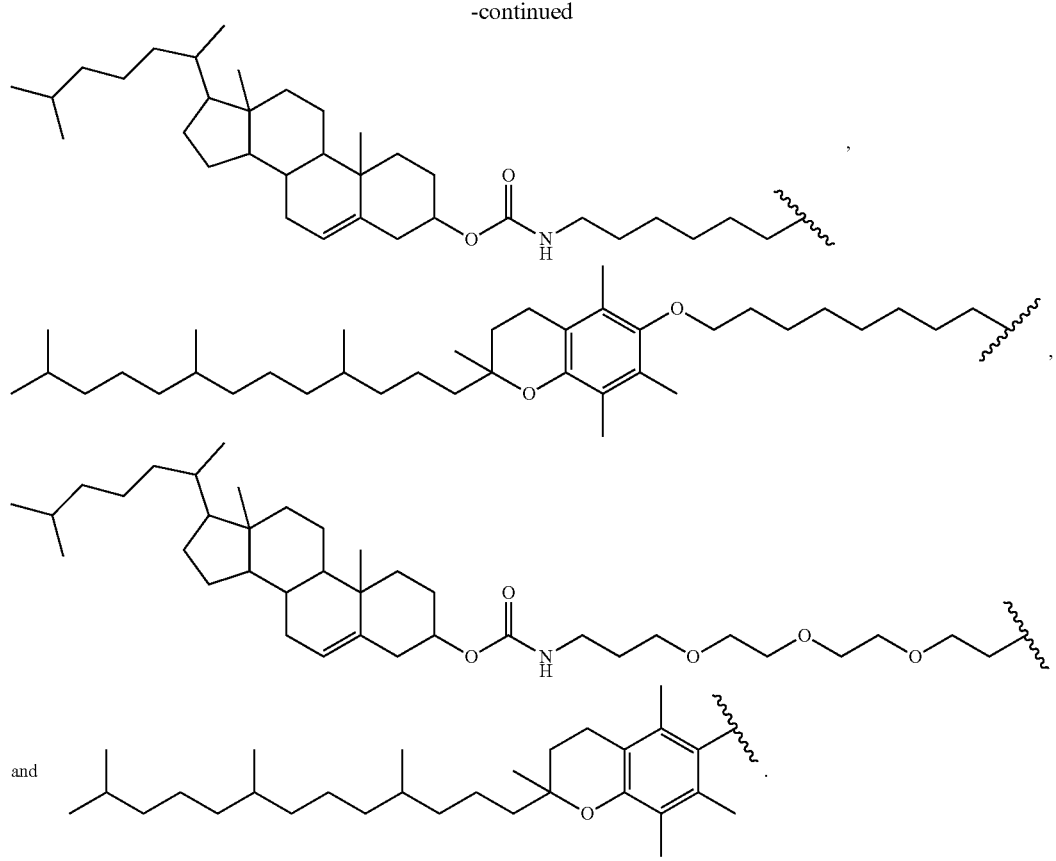

Usually, the hydrophobic group, R, does not contain a group of the following formula:

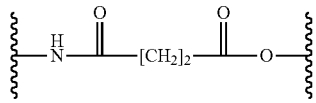

Often, the hydrophobic group, R, does not contain a group of the following formula:

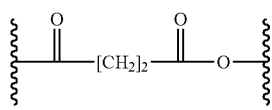

The hydrophobic group, R, typically does not contain a group of the following formula:

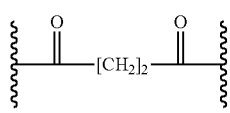

In some embodiments, the hydrophobic group, R, is a group of formula (III)

$$X-Y-Z- \qquad (III)$$

wherein:
Z is unsubstituted or substituted $C_{2-60}$ alkylene;
Y is N(R') or —C(O)N(R')—, wherein R' is H, unsubstituted or substituted $C_{1-4}$ alkyl or unsubstituted or substituted phenyl; and
X is H or unsubstituted or substituted $C_{1-200}$ alkyl.

Often, Z is covalently bonded directly to an oxygen atom of the phosphate group of the nucleotide at the 5' end of Tag. Alternatively, Z may be covalently bonded directly to an oxygen atom of a phosphate group at the 3' end of Tag, wherein another oxygen atom of the phosphate group at the 3' end of Tag is covalently bonded directly to the 3' ring carbon of the nucleotide at the 3' end of Tag.

Typically, when R is a group of formula (III):
Z is bonded to the 5' end of Tag and is unsubstituted or substituted $C_{4-20}$ alkylene;
Y is N(R') or —C(O)N(R')—, wherein R' is H, unsubstituted $C_{1-4}$ alkyl or unsubstituted phenyl; and
X is H or unsubstituted or substituted $C_{1-40}$ alkyl.

More typically, when R is a group of formula (III):
Z is bonded to the 5' end of Tag and is unsubstituted $C_{3-20}$ alkylene;
Y is —N(H)— or —C(O)N(H)—; and
X is H or unsubstituted $C_{4-30}$ alkyl. Typically, in these embodiments, Z is covalently bonded directly to an oxygen atom of the phosphate group of the nucleotide at the 5' end of Tag.

Advantageously, tracer compounds comprising a hydrophobic group, R, of formula (III) showed a high tendency to remain with fuel oil hydrocarbons even when extensively and vigorously water washed, and yet could easily be extracted from the fuel oil hydrocarbons for analysis, if required, using an aqueous buffer solution comprising surfactants.

The hydrophobic group, R, of formula (III), may for instance be:

bic group. As discussed above, the direct bond to the hydrophobic group is generally a covalent bond between the hydrophobic group and the 5' or 3' end of the principle strand, and it is usually a covalent bond between the hydrophobic group and the 5' end of the principle strand.

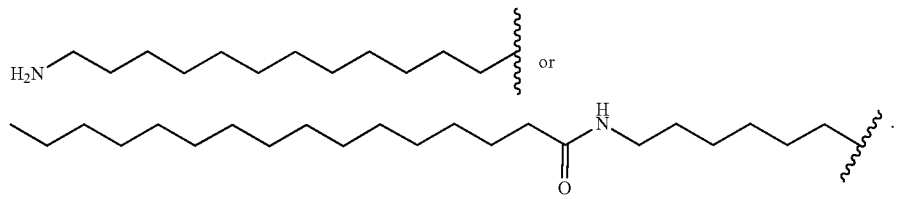

In another embodiment, the hydrophobic group, R, comprises a hydrophobic polymer. The polymer may be a synthetic conjugated polymer, which is hydrophobic.

R in this embodiment may be a polymer which is bonded to Tag directly, e.g. via a covalent bond. The polymer is often covalently bonded to the 5' end of Tag, usually to an oxygen atom of the terminal phosphate group at the 5' end of Tag.

Alternatively, the polymer may be bonded to Tag via a linker group, which may be a linker group, L, as defined hereinbefore. The linker is often covalently bonded to the 5' end of Tag, usually to an oxygen atom of the terminal phosphate group at the 5' end of Tag.

Accordingly, R may comprise said hydrophobic polymer and a linker group, L, as defined hereinbefore.

Any suitable polymer may be employed, as long as it is hydrophobic so that it may aid dissolution of the tracer compound into the apolar medium. Hydrophobic polymers are well known in the art and include, hydrocarbon polymers. Accordingly, the hydrophobic polymer may be a hydrocarbon polymer. The hydrocarbon polymer may, for example, be a hydrocarbon polymer which has a molecular weight of at least 1,800 Da. The hydrocarbon polymer may, for instance, be a polyolefin, for instance polyethylene, polypropylene, polymethylpentene, polybutene-1; or a polyolefin elastomer, such as, for example, polyisobutylene, ethylene propylene rubber, and ethylene propylene diene monomer (M-class) rubber.

Oligonucleotide

The oligonucleotide is generally deoxyribonucleic acid (DNA). Accordingly, the nucleotides present in the oligonucleotide are typically independently selected from: deoxyadenosine monophosphate (dAMP), deoxyguanosine monophosphate (dGMP), deoxythymidine monophosphate (dTMP) and deoxycytidine monophosphate (dCMP).

The oligonucleotide (denoted Tag in formula I) is generally single-stranded. However, as will be appreciated by the skilled person, a single stranded oligonucleotide may have one or more primers or probes hybridised thereto. Accordingly, depending on the nature of the composition in which the oligonucleotide is present, and in particular depending on whether or not the composition further comprises one or more additional oligonucleotides which have a sequence that is complementary to a sequence of nucleotides in Tag (for instance one or more primers or probes), the oligonucleotide Tag may comprise one or more regions of double stranded oligonucleotide. These are generally relatively short regions compared to the length of the oligonucleotide. However, in such cases, only one stand (which may be termed the "principal strand") will be bonded directly to the hydropho- The length of the oligonucleotide in the tracer compound is defined herein in terms of the number of nucleotides in the oligonucleotide strand which is bonded directly to the hydrophobic group. Thus, any further nucleotides which are hybridised to that strand (i.e. in cases where the oligonucleotide comprises one or more double stranded regions) are discounted; only the nucleotides in the principal strand are counted.

Typically, the length of the oligonucleotide (denoted Tag in formula I) is from 25 to 200 nucleotides. The length of the oligonucleotide may for instance be from 30 to 150 nucleotides, or for instance from 35 to 120 nucleotides. Often, however, the length of the oligonucleotide is from 40 to 110 nucleotides, for instance from 45 to 100 nucleotides, or for example from 50 to 90 nucleotides. The length of the oligonucleotide may for instance be from 60 to 80 nucleotides.

Generally, the oligonucleotide of the tracer compound comprises a unique sequence of nucleotides, which provides information about an apolar medium that is labelled with the tracer compound (a "labelled" or "tagged" apolar medium). The unique sequence of nucleotides may for instance denote a particular watercraft (e.g. a particular boat or ship, e.g. a particular cruise liner or oil tanker) so that an apolar medium which was tagged with the tracer compound on the watercraft can subsequently be identified as having been on that particular watercraft. More usefully, however, the unique sequence of nucleotides may denote a particular voyage of a particular watercraft. An apolar medium which was tagged with the tracer compound on the watercraft can then subsequently be identified as having been on that particular voyage of the watercraft. It is also envisaged that the unique sequence of nucleotides may denote a particular area within a particular watercraft, so that an apolar medium which was tagged with the tracer compound in that area of the watercraft can subsequently be identified as having been in that particular area of the watercraft. It is also envisaged that the unique sequence of nucleotides may denote a particular area within a particular watercraft, and a particular voyage of that particular watercraft. An apolar medium which was tagged with the tracer compound on the watercraft can then subsequently be identified as having been in that particular area of the watercraft on that particular voyage of the watercraft.

The unique sequence of nucleotides, which represents information about an apolar medium that is labelled (or is to be labelled) with the tracer compound, will of course vary depending on the information about the tagged apolar medium that is to be represented by that part of the sequence. For example, the unique sequence of nucleotides, which provides information about an apolar medium that is tagged with the tracer compound, will generally vary depending on the particular watercraft in which the tracer compound is to be deployed. It will also generally vary depending on the particular voyage of the watercraft in which the tracer compound is to be deployed. It can also vary depending on the particular area within a given watercraft in which the tracer compound is to be deployed. A given watercraft going on a particular voyage may therefore have a plurality of different tracer compounds on board, each one being deployed in a different area of the watercraft. In such a case, the oligonucleotide of the tracer in each different area will comprise a unique sequence of nucleotides that denotes the particular area of the watercraft in which that tracer is deployed, and the oligonucleotides in all of the areas will also denote the particular watercraft, and the particular voyage.

The unique sequence of nucleotides in the oligonucleotide, which provides information about an apolar medium that is labelled (or is to be labelled) with the tracer compound, is typically in a central region of the oligonucleotide (as opposed to at either of the 5' or 3' ends of the oligonucleotide). This is because the oligonucleotide generally also comprises a sequence of nucleotides at or near the 5' end, and a sequence of nucleotides at or near the 3' end, which carry predetermined sequences that will recognise appropriate complementary primers for use in PCR amplification and in sequencing of the PCR amplified nucleic acid.

The oligonucleotide (denoted Tag in formula I) may for instance be represented as follows:

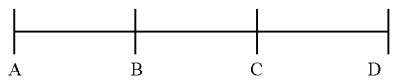

wherein the regions AB and CD respectively comprise predetermined sequences that will recognise appropriate complementary primers for use in amplification (e.g. PCR amplification) and optionally in sequencing of the amplified nucleic acid; and the region BC comprises a unique sequence of nucleotides that represents information about the apolar medium that is labelled (or to be labelled) with the tracer compound.

The regions AB and CD generally will not vary from watercraft to watercraft, or from voyage to voyage, and will not change depending upon a particular area of the watercraft in which they are deployed. Rather, they will generally be constant for all tracer compounds in a particular batch, or "library", of tracer compounds to be employed in accordance with the present invention. Each of the regions AB and CD of the oligonucleotide typically has a length of from 8 to 50 nucleotides, for instance from 10 to 40 nucleotides, or for instance from 15 to 30 nucleotides.

The region BC, on the other hand, comprises a unique sequence of nucleotides that represents information about the apolar medium that is labelled (or is to be labelled) with the tracer compound. This is the region that gives each tracer compound its unique, characteristic signal, and will vary as the information about apolar medium to be labelled with the tracer compound varies. The uniqueness of the sequence of nucleotides that represents information about the apolar medium is generally known only to the individuals using the tracer in accordance with the invention, thereby guaranteeing security of the information.

The region BC may for instance comprise a sequence of nucleotides which identifies the apolar medium as:
having been on board a particular watercraft;
having been on board a particular watercraft during a particular voyage;
having been present in a particular area, tank, container or bunker within a particular watercraft; or
having been present in a particular area, tank, container or bunker within a particular watercraft during a particular voyage.

The region BC of the oligonucleotide may have a length of, for instance, from 5 to 120 nucleotides. It may for instance have a length of from 10 to 80 nucleotides, or for example from 15 to 50 nucleotides, for instance from 20 to 40 nucleotides. Indeed, if the BC region is 10 nucleotides in length then with the four bases available for a DNA molecule, there will be $1.048 \times 10^6$ unique molecules capable of being synthesised. If the BC region is 15 bases long, then $1.07 \times 10^9$ unique molecules can be synthesised. If the BC region is 30 bases long, $1.15 \times 10^{18}$ unique molecules can be synthesised. Each of these unique molecules can potentially represent different information about an apolar medium to be labelled.

SEQ ID NO: 1, which contains 60 nucleotides, is an example of a suitable oligonucleotide sequence that may be employed in accordance with the invention.

The oligonucleotide (denoted Tag in formula I) is often referred to herein as an "identifiable oligonucleotide" on the basis that it can readily be identified by performing standard techniques on the tracer compound.

The identity of the oligonucleotide of the tracer compound can readily be determined by (a) amplifying the oligonucleotide; and (b) sequencing the amplified oligonucleotide.

The oligonucleotide may be amplified by performing PCR (the polymerase chain reaction) on the tracer compound. Accordingly, step (a) may comprise performing PCR on the tracer compound. PCR and sequencing are both very well known techniques. The PCR may for instance be qPCR (quantitative polymerase chain reaction), which is also well known.

Often, analysing the identifiable oligonucleotide of the tracer compound to determine the identity of the oligonucleotide comprises:

(a) amplifying the oligonucleotide in the presence of an intercalating reporter dye to determine that an oligonucleotide is present;
(b) optionally further amplifying the oligonucleotide; and
(c) sequencing the amplified oligonucleotide and thereby determining the identity of the oligonucleotide.

The amplifying in steps (a) and (b) is typically achieved by performing PCR, for instance qPCR. The sequencing in step (c) may be by any suitable method. Methods for sequencing oligonucleotides are well known in the art.

Composition

Generally, the apolar medium in the composition of the invention is immiscible with water. The apolar medium is typically a liquid (at SATP) that is immiscible with water. The composition is typically therefore a liquid composition.

The composition of the invention often further comprises water. For example, the composition of the invention may comprise oily waste water, comprising the apolar medium, the tracer compound, and water. The oily waste water may be in, or from, a bilge area or a container for waste (e.g. a sludge tank) in a watercraft (such as a ship, e.g. a cruise liner or an oil tanker). Alternatively, the composition of the invention may comprise a mixture of (i) apolar medium, (ii)

the tracer compound and (iii) water (e.g. seawater) into which the labelled apolar medium has been spilled. Thus, in one embodiment the water in the composition of the invention is seawater. The water in the composition of the invention may therefore be water having a salinity of at least 3.0% (i.e. at least 30 g/L) or for instance at least about 3.5% (i.e. at least about 3.5 g/L).

When the composition of the invention further comprises water, the water in the composition is generally immiscible with the apolar medium. The water and the apolar medium typically therefore form separate phases in the composition: a water phase (also termed an aqueous phase) and an apolar phase. The tracer compound is present in the apolar phase. For instance it may be dissolved, dispersed or suspended in the apolar phase. Usually it is dissolved in the apolar phase. Indeed, generally, owing to the presence of the hydrophobic group in the tracer compound, which group is denoted R in formula I, the tracer compound is soluble in the apolar phase. Accordingly, in the composition of the invention, the tracer compound is typically dissolved, or if not dissolved then dispersed or suspended, in the apolar medium. Usually, the tracer compound is dissolved in the apolar medium.

The tracer compound is generally more soluble in the apolar phase than in the aqueous phase, such that a greater concentration of the tracer compound dissolves in the apolar medium than in the water. The distribution ratio ($K_d$), which is equal to the concentration of the tracer compound in the apolar phase divided by its concentration in the aqueous phase, is typically greater than 1, for instance at least 10, and is often at least 100. It may for instance be at least 1,000. $K_d$ may for instance be from greater than 1 to 10,000, or for example from 2 to 1,000, or from 5 to 500.

Often, therefore, the composition of the invention further comprises water, wherein the apolar medium is immiscible with the water and the tracer compound is dissolved in the apolar medium. Typically, the distribution ratio, $K_d$, in the composition is as defined above.

The invention further provides a composition which comprises (i) an apolar medium, and (ii) a plurality of tracer compounds, wherein each tracer compound in the plurality comprises a hydrophobic group and an oligonucleotide, and wherein the oligonucleotide of each tracer compound in the plurality comprises a different unique sequence of nucleotides.

The apolar medium, and each of the tracer compounds in the plurality (and the hydrophobic group and oligonucleotide therein) may be as defined anywhere herein.

However, the oligonucleotide of each tracer compound in the plurality comprises a different unique sequence of nucleotides. Typically, each of the different unique sequences of nucleotides will represent different information. For instance, each of the different unique sequences of nucleotides will typically provide a different piece of information about the apolar medium in the composition. These may be different pieces of information about the history of the apolar medium in terms of its whereabouts, e.g. that is has been on board a ship or other kind of watercraft, in a particular area on a particular watercraft, and/or on a particular voyage of a particular watercraft. The tracer compounds may also provide information about the mixing together of differently-tagged apolar media to form the apolar medium in the composition. The plurality of tracer compounds may allow detailed information to be built up about the history of a particular composition, for instance that is has been on board more than one particular voyage, that the apolar medium contains different components from different batches or for instance that the apolar medium is contaminated with one or more batches of apolar media from a different, previous voyage or from a different area in the watercraft.

Often, the oligonucleotide of each tracer compound in the plurality further comprises one or more sequences that do not vary from tracer compound to tracer compound in the plurality. These are typically sequences that will recognise complementary primers for use in amplification (e.g. PCR amplification) or in sequencing of the amplified nucleic acid.

Process for Producing Composition

The composition of the invention may be produced by treating a precursor composition comprising an apolar medium with the tracer compound. This may be referred to as labelling or tagging the apolar medium with the tracer compound. The tracer compound may be added to the apolar medium in solid form, or the tracer compound may first be dissolved or suspended in a solvent, for instance an organic solvent, e.g. a $C_{5-10}$ hydrocarbon solvent or tetrahydrofuran, and then added to the apolar medium. Typically, the tracer compound then dissolves or otherwise becomes dispersed or suspended in the apolar medium. Usually, it dissolves in the apolar medium. Mixing or agitation of the apolar medium and the tracer compound may aid dissolution.

Accordingly, the invention provides a process for producing a composition which comprises an apolar medium and a tracer compound, which tracer compound comprises a hydrophobic group and an oligonucleotide, which process comprises: treating a precursor composition comprising an apolar medium with said tracer compound.

The composition of the invention may further comprise water. Such compositions which further comprise water may be prepared either by treating a composition comprising water and an apolar medium with the tracer compound, or by treating water with a composition comprising the apolar medium and the tracer compound.

Accordingly, in the process of the invention for producing a composition which comprises an apolar medium and a tracer compound, the above-mentioned precursor composition may further comprise water; or the process may further comprise treating the resulting composition with water. A composition which comprises the apolar medium, the tracer compound, and which further comprises water, is thereby produced.

As discussed above in relation to the composition of the invention, the water is generally immiscible with the apolar medium and the tracer compound is typically dissolved in the apolar medium.

The tracer compound itself may be produced by (i) synthesising the desired oligonucleotide, Tag, and then (ii) coupling the hydrophobic group, R, to the oligonucleotide. Regarding (i), oligonucleotide synthesis methods are very well known in the art. As for (ii), methods for modifying oligonucleotides by coupling compounds, including substituted or unsubstituted hydrocarbons, to the 5' or 3' ends of an oligonucleotide, are also very well known. Examples of some common oligonucleotide labelling reactions are: reaction of a phosphoramidite derivative of the labelling group with the oligonucleotide during solid phase synthesis; reaction of a free amino group on an oligonucleotide with an N-hydroxysuccinimide ester or other activated carboxyl group such as an isothiocyanate derivative of a luminescent dye or enzyme; reaction of a thiol-modified oligonucleotide with an α,β-unsaturated ketone attached to a luminescent label or activated enzyme; reaction of an amino-modified nucleoside triphosphate with a carboxy-activated label, and subsequent incorporation of the labelled triphosphate into DNA during PCR or other enzyme-catalysed DNA extension reaction; reaction of an alkyne-modified oligonucleotide with an azide-modified label, to form a triazole linkage (click chemistry); reaction of an azide-modified oligonucleotide with an alkyne-modified label, to form a triazole linkage (click chemistry). Such methods are discussed in more detail on the website of ATDBio (www.atdbio.com), from whom the modified oligotides employed in the Example hereinbelow were obtained, and are also well known.

A Watercraft with a Composition on Board

The invention also provides a watercraft having a composition on board, which composition comprises an apolar medium and a tracer compound, which tracer compound comprises a hydrophobic group and an oligonucleotide.

The composition, apolar medium and a tracer compound, may be as defined anywhere herein.

The term "watercraft", as used herein, takes its normal meaning, and encompasses any water-borne vehicle including, but not limited to, a ship, a boat, a hovercraft and a submarine. Typically, the watercraft is a boat or a ship. It is often a marine vessel. It is typically a ship, for instance a merchant ship. It may for example be an oil tanker or a cargo ship. The ship may alternatively, for instance, be a cruise liner.

The composition may be present in any part of the watercraft that would normally comprise an apolar medium that could be labelled with a tracer compound in accordance with the invention. The oligonucleotide of the tracer compound of the composition may comprise a unique sequence of nucleotides which identifies that area of the watercraft. The unique sequence of nucleotides will generally identify the watercraft itself and will typically also identify a particular voyage of the watercraft (so that this information can be found out if and when the tracer is recovered after an illegal discharge of the composition from the watercraft).

The composition may for instance be present in a cargo container, or a cargo tank, in the watercraft. This may be the case, for instance, if the apolar medium which is labelled with the tracer compound is cargo to be transported aboard the watercraft. The apolar medium cargo may for instance be a petroleum product or an oil. For instance it may be gasoline, diesel, crude oil or fuel oil.

Another possibility is that the composition is present in a bunker within the watercraft. As will be understood by the skilled person, the term "bunker", refers to an on-board fuel tank in a watercraft, and particularly to an on-board fuel tank in a ship. The composition may be present in the bunker if the apolar medium which is labelled with the tracer compound is fuel for the watercraft. It may for instance be fuel oil, for instance marine diesel, intermediate fuel oil or heavy fuel oil.

Yet another possibility is that the composition is present in a bilge area of the watercraft. In this embodiment, the composition will further comprise water.

As will be understood by the skilled person, the bilge is the bottom part of the inside of a ship or boat. This is generally the lowest compartment on a ship or boat, below the waterline, where the two sides meet at the keel. It collects waste liquids that leak and drain down through the ship or boat. The liquid in the bilge is primarily aqueous and is often therefore referred to as "bilge water". However, oil leakage in the engine room is also collected in bilge wells, as well as for example fuel, solvents, chemicals, pitch, particles, and other materials, to produce oily waste water. This oily water mixture is then transferred to a bilge tank. Discharge of bilge liquids (e.g. from bilge tanks) may be restricted and for commercial vessels is regulated.

Yet another possibility is that the composition is present in a container for waste within the watercraft, for instance in a bilge tank, a slop tank, a sludge tank, or an oily water separator (O.W.S) sludge tank. In this embodiment, the composition will typically further comprise water.

Slop tanks are present on board watercraft, particularly tankers, to store oily water mixture from cargo tank washing.

A sludge tank is typically located in the engine room of a watercraft. The sludge tank is generally used to store sludge produced after treating fuel, lubricant oil and/or hydraulic oil through purifiers.

An oily water separator (O.W.S) sludge tank contains oil which has been separated from water (for instance from bilge water) using an oily water separator.

Accordingly, in one embodiment the composition is present in a cargo container or cargo tank within the watercraft, or in a bunker within the watercraft.

In another embodiment the composition further comprises water and the composition is present in container for waste within the watercraft, for instance in a bilge area, a bilge tank, a slop tank, a sludge tank or an oily water separator sludge tank.

The oligonucleotide of the tracer compound of the composition may comprise a unique sequence of nucleotides which identifies that area of the watercraft. The unique sequence of nucleotides will generally identify the watercraft itself and will typically also identify a particular voyage of the watercraft (corresponding to a voyage of the watercraft during which the composition is on board the watercraft).

Accordingly, in one embodiment, the composition is present in a cargo container, a cargo tank, a bunker, a bilge area, a bilge tank, a slop tank, a sludge tank or an oily water separator sludge tank within the watercraft and the oligonucleotide of the tracer compound of the composition comprises a unique sequence of nucleotides which identifies that cargo container, cargo tank, bunker, bilge area, bilge tank, slop tank, sludge tank or oily water separator sludge tank of the watercraft. The unique sequence of nucleotides will generally identify the watercraft itself and will typically also identify a particular voyage of the watercraft (corresponding to a voyage of the watercraft during which the composition is on board the watercraft).

Typically the oligonucleotide of the tracer compound of the composition on board the watercraft comprises a sequence of nucleotides which identifies the apolar medium as:

having been on board said watercraft;

having been on board said watercraft during a particular voyage;

having been present in a particular area, tank, container or bunker within said watercraft; or having been present in a particular area, tank, container or bunker within said watercraft during a particular voyage.

More than one type of tracer compound as defined herein may be present in the watercraft, for identifying apolar materials as having been present in that area of the watercraft.

Accordingly, the watercraft may comprise a plurality of compositions on board, each of which comprises an apolar medium and a tracer compound, which tracer compound comprises a hydrophobic group and an oligonucleotide, wherein each composition in the plurality is present in a different area of the watercraft, and wherein the oligonucleotide of the tracer compound of each composition in the plurality comprises a unique sequence of nucleotides which identifies that area of the watercraft. Usefully, the unique sequence will typically also identify a particular voyage of the watercraft. An apolar medium can subsequently therefore be identified as having come from a particular area or compartment within a watercraft (e.g. ship) during a particular voyage of that watercraft, allowing this information to be found out if and when the tracer is recovered after an illegal discharge from the watercraft. Each composition in the plurality may be present in a different area of the watercraft selected from cargo containers, cargo tanks, bunkers, containers for waste, bilge areas, bilge tanks, slop tanks, sludge tanks and oily water separator sludge tanks.

The plurality of compositions may for instance comprise a first composition in a first area of the watercraft, a second composition in a second area of the watercraft, and a third composition in a third area of the watercraft, wherein each of the first, second and third areas are different and are selected from cargo containers, cargo tanks, bunkers, containers for waste, bilge areas, bilge tanks, slop tanks, sludge tanks and oily water separator sludge tanks.

Methods of Labelling an Apolar Medium (and Subsequent Identification)

The invention provides a method of labelling an apolar medium to be carried on board a watercraft, which method comprises:

(i) treating a composition comprising an apolar medium with a tracer compound, wherein the tracer compound comprises a hydrophobic group and an identifiable oligonucleotide, and thereby producing a labelled apolar medium, wherein the labelled apolar medium comprises the apolar medium and the tracer compound.

The invention also provides a method of labelling an apolar medium and subsequently identifying information about the apolar medium following discharge of the labelled apolar medium from a watercraft into water, the method comprising:

(i) treating a composition comprising an apolar medium with a tracer compound, wherein the tracer compound comprises a hydrophobic group and an identifiable oligonucleotide, and thereby producing a labelled apolar medium, wherein the labelled apolar medium comprises the apolar medium and the tracer compound, and wherein the labelled apolar medium is present on board a watercraft for a period of time;

(ii) after a discharge of said labelled apolar medium from the watercraft into the water, obtaining a sample comprising labelled apolar medium that was discharged;

(iii) retrieving the tracer compound from said sample;

(iv) analysing the identifiable oligonucleotide of the tracer compound to determine the identity of the oligonucleotide; and (v) using the identity of the oligonucleotide to identify information about the apolar medium.

In these methods of the invention, the apolar medium and the tracer compound may be as further defined anywhere herein.

In the labelled apolar medium, the tracer compound is typically dissolved in the apolar medium.

Step (i) in these methods of the invention may comprise treating the composition comprising the apolar medium with the tracer compound when the composition is on board the watercraft. For instance, the tracer compound may be introduced into a cargo container, cargo tank, bunker, container for waste, bilge area, bilge tank, slop tank, sludge tank or oily water separator sludge tank in the watercraft. This area of the watercraft may already contain the composition comprising the apolar medium to be labelled, or the apolar medium to be labelled may not yet be present in the area when the tracer compound is introduced, and may subsequently be added. For example, an "inspector" from a recognised organisation (e.g. a class surveyor, or an independent body who could oversea process and verify addition of the tracer) may spray the tracer over the bilges or into the waste containers.

As will be understood by the skilled person, if the composition comprising the apolar medium is present in a bilge area or a container for waste, for instance a bilge area, bilge tank, slop tank, sludge tank or oily water separator sludge tank, then the composition comprising the apolar medium will generally further comprise water. The composition comprising the apolar medium to which the tracer is added may for instance be oily waste water. The hydrophobic nature of the tracer ensures that the tracer will remain in the oily (apolar) phase rather than be leached out into the water, so that the apolar medium may be effectively tagged.

If on the other hand the composition comprising the apolar medium is present in a bunker or cargo container, the composition comprising the apolar medium may be a relatively pure product, such as a hydrocarbon petroleum product or fuel oil, that will contain little or no water. However, the apolar medium may subsequently leak out into the waste areas of the watercraft that do contain water, and again the hydrophobic nature of the tracer ensures that the tracer will remain in the oily (apolar) phase rather than be leached out into the water phase, so that the apolar medium is effectively tagged. Also, of course, in the event of spillage of cargo overboard or illegal discharge of the apolar medium into the water, the apolar medium will be effectively tagged.

Step (i) may alternatively comprise treating the composition comprising the apolar medium with the tracer compound prior to the composition being brought on board the watercraft. For instance, a hydrocarbon petroleum product to be transported by the watercraft as cargo may be tagged with the tracer prior to loading the cargo. Similarly, a fuel to be supplied to a bunker on board the vessel may be tagged prior to the bunkering process.

Step (i) in the above-defined methods of labelling an apolar medium, of treating the composition comprising the apolar medium with the tracer compound, may for instance comprise: introducing the tracer compound into a bilge area of the watercraft, before, during or after the composition comprising the apolar medium is disposed in said bilge area.

Another possibility is that step (i) in the above-defined methods, of treating the composition comprising the apolar medium with the tracer compound, comprises introducing the tracer compound into a cargo tank or cargo container on the watercraft, before, during or after a composition comprising the apolar medium is disposed in said cargo tank or cargo container.

Another possibility is that step (i) in the above-defined methods, of treating the composition comprising the apolar medium with the tracer compound, comprises introducing the tracer compound into a cargo composition comprising the apolar medium prior to introducing the cargo composition into a cargo tank or cargo container on the watercraft. This task may for instance be performed by an "inspector" from a recognised organisation (e.g. a class surveyor, or an independent body who could oversea process and verify addition of the tracer).

Another possibility is that step (i) in the above-defined methods, of treating the composition comprising the apolar medium with the tracer compound, comprises introducing the tracer compound into a conduit (e.g. pipe) through which a cargo composition comprising the apolar medium is loaded (e.g. pumped) onto the watercraft.

Another possibility is that step (i) in the above-defined methods, of treating the composition comprising the apolar medium with the tracer compound, comprises introducing the tracer compound into a waste container on the watercraft, for instance into a bilge tank, slop tank, sludge tank or oily water separator sludge tank, before, during or after a composition comprising the apolar medium is disposed in said waste container.

Another possibility is that step (i) in the above-defined methods, of treating the composition comprising the apolar medium with the tracer compound, comprises introducing the tracer compound into a waste composition comprising the apolar medium and water, prior to introducing the waste composition into a waste container (for instance into a bilge tank, slop tank, sludge tank or oily water separator sludge tank) on the watercraft.

Another possibility is that step (i) in the above-defined methods, of treating the composition comprising the apolar medium with the tracer compound, comprises introducing the tracer compound into a bunker on the watercraft, before, during or after a fuel composition comprising the apolar medium is introduced into the bunker.

The tracer compound may for instance be dripped-in during the bunker distributor process using dosing pumps, which guarantees good mixing. The tracer compound may alternatively be introduced into a central manifold and distributed into multiple tanks. Another possibility is that the tracer compound may be introduced prior to bunkering via the sounding pipe, or introduced into the tank at the start, so that loading of the bunkers causes good mixing of the tracer into the fuel, and a high probability that it will be marked entirely.

Another possibility is that step (i) in the above-defined methods, of treating the composition comprising the apolar medium with the tracer compound, comprises introducing the tracer compound into a fuel composition comprising the apolar medium prior to introducing the fuel composition into a bunker on the watercraft.

After the labelling of the apolar medium with the tracer compound, the tracer compound can be used to identify crucial information about the history of the apolar medium in the event of a discharge (e.g. an illegal discharge or a spill) of the labelled apolar medium from the watercraft into the water. The apolar medium discharged from the watercraft into water may be in the form of waste fuel, which may for instance be marine diesel, intermediate fuel oil, or heavy oil; fuel by-products or residues; wasted cargo, which may for example be a petroleum product or an oil; a lubricant oil; a hydraulic oil, or a mixture of any of these materials. Such materials may have been disposed directly into a waste container or a sludge tank (which will generally also contain waste water), or may first been disposed in a bilge area (which will also generally contain a high volume of water), and then subsequently transferred to a waste container or bilge tank. The apolar medium disposed from the vessel into the water, typically from a bilge area, waste container, bilge tank, sludge tank or slop tank, will generally be a mixture of water and the apolar medium. The tracer compound employed in the present invention is largely if not completely retained in the apolar phase, however, and does not leach out into the aqueous phase in these areas of the watercraft, owing to the hydrophobic group in the tracer compound. It also does not leach into the water in the event of discharge from the watercraft into the water, for instance into the sea.

Thus, the above-defined method of labelling an apolar medium and subsequently identifying information about the apolar medium following discharge of the labelled apolar medium from a watercraft into water, further comprises a step (ii) of:

after a discharge of said labelled apolar medium from the watercraft into the water, obtaining a sample comprising labelled apolar medium that was discharged.

A sample comprising the labelled apolar medium that was discharged from the watercraft (e.g. boat or ship) into the water (e.g. the sea) may be obtained by known methods. For instance, the sample may be obtained by dangling a sampler (typically comprising an absorbent material) from an aircraft such as a helicopter into the water in the area of discharge. Alternatively it is known to use miniature submarines for sampling in areas of discharge or spillage. The sample comprising labelled apolar medium that was discharged will generally comprise water, the apolar medium and the tracer compound. As discussed hereinbefore, generally the apolar medium and the water are immiscible and therefore form separate phases, and the tracer compound is present in the apolar phase. It is typically dissolved in the apolar medium.

Once the sample comprising labelled apolar medium that has been discharged from a watercraft into the water has been obtained, the next step (iii) of the above-defined method of labelling an apolar medium and subsequently identifying information about the apolar medium, and indeed step (iii) of the method defined below of identifying information about an apolar medium after discharge of the apolar medium from a watercraft into the water, comprises:

retrieving the tracer compound from said sample.

The invention further comprises a method of identifying information about an apolar medium after discharge of the apolar medium from a watercraft into the water, which method comprises: (iii) retrieving a tracer compound from a sample comprising a labelled apolar medium that has been discharged from a watercraft into the water, wherein the labelled apolar medium comprises an apolar medium and a tracer compound, wherein the tracer compound comprises a hydrophobic group and an identifiable oligonucleotide; and (iv) analysing the identifiable oligonucleotide of the tracer compound to determine the identity of the oligonucleotide. This method optionally further comprises: (v) using the identity of the oligonucleotide to identify information about the apolar medium.

Step (iii), in the above defined method of labelling an apolar medium and subsequently identifying information about the apolar medium following discharge of the labelled apolar medium from a watercraft into water, and also in the above defined method of identifying information about an apolar medium after discharge of the apolar medium from a watercraft into the water, typically comprises: separating the apolar medium from the sample comprising the labelled apolar medium, and extracting the tracer compound from the separated labelled apolar medium.

As discussed above, the sample comprising a labelled apolar medium that has been discharged, generally comprises water, the apolar medium and the tracer compound. Typically the tracer compound is present in, and is usually dissolved in, the apolar medium. The water in the sample may be seawater. The water in the composition of the invention may therefore be water having a salinity of at least 3.0% (i.e. at least 30 g/L) or for instance at least about 3.5% (i.e. at least about 3.5 g/L).

Usually, therefore, step (iii) comprises separating at least some of the apolar medium from water in the sample comprising the labelled apolar medium, and extracting the tracer compound from the separated labelled apolar medium.

The water and the apolar medium typically form separate liquid phases in the composition: a water phase (also termed an aqueous phase) and an apolar phase. The step of separating at least some of the apolar medium from water in the sample comprising the labelled apolar medium, can therefore be performed using known laboratory techniques for separating two immiscible liquid phases from one another, such as for instance by using a separation funnel.

The step of extracting the tracer compound from the separated labelled apolar medium typically comprises contacting the separated labelled apolar medium with an aqueous extractant composition which comprises water and a surfactant. Any suitable surfactant for aiding dissolution of the tracer compound in the aqueous phase may be employed. Cationic surfactants may for instance be employed in the aqueous phase to aid extraction of the nucleic acid from the apolar phase.

Typically, however, the surfactant is a non-ionic surfactant. The non-ionic surfactant may alternatively be referred to as a non-ionic detergent. The terms "non-ionic surfactant" and "non-ionic detergent" are interchangeable, as used herein, as are the terms "surfactant" and "detergent".

Thus, the step of extracting the tracer compound from the separated labelled apolar medium typically comprises contacting the separated labelled apolar medium with an aqueous extractant composition which comprises water and a non-ionic surfactant.

The non-ionic surfactant may for instance comprise a non-ionic surfactant, or a mixture of two or more (for instance two or three) non-ionic surfactants, selected from: fatty acid esters of polyhydroxy compounds, fatty alcohol ethoxylates, alkylphenol ethoxylates, ethoxylated amines, fatty acid amides, poloxamers, alkyl polyglycosides (APGs), alkyl glycosides, alkyl thioglycosides and amine oxide non-ionic surfactants.

The fatty acid esters of polyhydroxy compounds may for instance be selected from fatty acid esters of sorbitan, fatty acid esters of ethoxylated sorbitan (polysorbates), fatty acid esters of glycerol, and fatty acid esters of sucrose.

The fatty acid esters of sorbitan and fatty acid esters of ethoxylated sorbitan (polysorbates) may for instance be selected from compounds of formula (X)

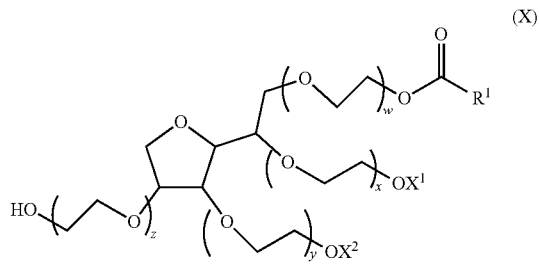

wherein
w is 0 or an integer of from 1 to 20;
x is 0 or an integer of from 1 to 20;
y is 0 or an integer of from 1 to 20;
z is 0 or an integer of from 1 to 20;
$R^1$ is $C_{8-30}$ hydrocarbyl;
$X^1$ is H or $C(O)R^{11}$, wherein $R^{11}$ is $C_{8-30}$ hydrocarbyl; and
$X^2$ is H or $C(O)R^{12}$, wherein $R^{12}$ is $C_{8-30}$ hydrocarbyl.
$R^1$ in formula (X) is typically unsubstituted $C_{8-30}$ alkyl or unsubstituted $C_{5-30}$ alkenyl. For instance, $R^1$ in formula (X) may be unsubstituted $C_{8-20}$ alkyl or unsubstituted $C_{8-20}$ alkenyl. $R^1$ in formula (X) may for instance be unsubstituted $C_{11}$ alkyl (e.g. to form a laurate group), unsubstituted $C_{15}$ alkyl (e.g. to form a palmitate group), unsubstituted $C_{17}$ alkyl (e.g. to form a stearate group), or unsubstituted $C_{17}$ alkenyl (e.g. to form an oleate group).

$R^{11}$ in formula (X) is typically unsubstituted $C_{8-30}$ alkyl or unsubstituted $C_{8-30}$ alkenyl. For instance, $R^{11}$ in formula (X) may be unsubstituted $C_{8-20}$ alkyl or unsubstituted $C_{8-20}$ alkenyl. $R^1$ in formula (X) may for instance be unsubstituted $C_{11}$ alkyl (e.g. to form a laurate group at $X^1$), unsubstituted $C_{15}$ alkyl (e.g. to form a palmitate group at $X^1$), unsubstituted $C_{17}$ alkyl (e.g. to form a stearate group at $X^1$), or unsubstituted $C_{17}$ alkenyl (e.g. to form an oleate group at $X^1$).

$R^{12}$ in formula (X) is typically unsubstituted $C_{8-30}$ alkyl or unsubstituted $C_{8-30}$ alkenyl. For instance, $R^{12}$ in formula (X) may be unsubstituted $C_{8-20}$ alkyl or unsubstituted $C_{8-20}$ alkenyl. $R^{12}$ in formula (X) may for instance be unsubstituted $C_{11}$ alkyl (e.g. to form a laurate group at $X^2$), unsubstituted $C_{15}$ alkyl (e.g. to form a palmitate group at $X^2$), unsubstituted $C_{17}$ alkyl (e.g. to form a stearate group at $X^2$), or unsubstituted $C_{17}$ alkenyl (e.g. to form an oleate group at $X^2$).

The sum of w, x, y and z is in some embodiments from 15 to 25. Typically, for instance, none of w, x, y and z is 0 (i.e. each of w, x, y and z is an integer of from 1 to 20) and the sum of w, x, y and z is from 15 to 25. Usually, in these embodiments where the sum of w, x, y and z is from 15 to 25, $X^1$ and $X^2$ are both H. $R^1$ is as defined above.

Often, the sum of w, x, y and z is 20. Typically, for instance, none of w, x, y and z is 0 (i.e. each of w, x, y and z is an integer of from 1 to 20) and the sum of w, x, y and z is 20. Usually, in these embodiments where the sum of w, x, y and z is 20, $X^1$ and $X^2$ are both H. $R^1$ is as defined above. Often, $R^1$ is unsubstituted $C_{8-20}$ alkyl or unsubstituted $C_{5-20}$ alkenyl. $R^1$ in formula (X) may for instance be unsubstituted $C_{11}$ alkyl (e.g. to form a laurate group, as in the compound polyoxyethylene (20) sorbitan monolaurate, known as "Tween 20" or "Polysorbate 20"), unsubstituted $C_{15}$ alkyl (e.g. to form a palmitate group, as in the compound polyoxyethylene (20) sorbitan monopalmitate, known as "Tween 40" or "Polysorbate 40"), unsubstituted $C_{17}$ alkyl (e.g. to form a stearate group, as in the compound polyoxyethylene (20) sorbitan monostearate, known as "Tween 60" or "Polysorbate 60"), or unsubstituted $C_{17}$ alkenyl (e.g. to form an oleate group, as in the compound polyoxyethylene (20) sorbitan monooleate, known as "Tween 80" or "Polysorbate 80"). The compound of formula (X) may for instance be Tween 20, Tween 40, Tween 60 or Tween 80. Preferably, however, the compound of formula (X) is Tween 20, i.e. polyoxyethylene (20) sorbitan monolaurate.

Alternatively, w, x, y and z in the compound of formula (X) may all be 0. When w, x, y and z are all 0, it may be the case that $X^1$ is $C(O)R^{11}$ and $X^2$ is $C(O)R^{12}$. $R^{11}$ and $R^{12}$ may each independently be as defined above. Often in this embodiment, however, $R^1$, $R^{11}$ and $R^{12}$ are the same, e.g. as defined above for $R^1$ in formula (X). For instance, $R^1$, and $R^{12}$ may all be unsubstituted $C_{8-20}$ alkyl or unsubstituted $C_{8-20}$ alkenyl. Thus, $R^1$, $R^{11}$ and $R^{12}$ may all, for instance, be unsubstituted $C_{17}$ alkyl. Thus, the compound of formula (X) may be sorbitan tristearate.

Alternatively, when w, x, y and z are all 0, it may be the case that $X^1$ and $X^2$ are both H. $R^1$ is as defined above. The compound of formula (X) may for instance be sorbitan monolaurate or sorbitan monostearate.

The fatty acid esters of glycerol may for instance be selected from monoesters of glycerol and a fatty acid of formula $R^2COOH$, wherein $R^2$ is $C_{8-30}$ hydrocarbyl and $R^2$ is more typically unsubstituted $C_{8-30}$ alkyl or unsubstituted $C_{8-30}$ alkenyl, for instance unsubstituted $C_{5-20}$ alkyl. The fatty acid esters of glycerol may for instance be selected from glycerol monostearate and glycerol monolaurate.

The fatty acid esters of sucrose may for instance be selected from monoesters of sucrose and a fatty acid of formula $R^3COOH$, wherein $R^3$ is $C_{8-30}$ hydrocarbyl and $R^3$ is more typically unsubstituted $C_{8-30}$ alkyl or unsubstituted $C_{8-30}$ alkenyl, for instance unsubstituted $C_{5-20}$ alkyl. The fatty acid esters of sucrose may for instance be selected from sucrose monostearate and sucrose monolaurate.

The fatty alcohol ethoxylates may for instance be selected from compounds of formula $HO(CH_2CH_2O)_nR^{20}$ wherein n is from 3 to 15 and $R^{20}$ is $C_{8-30}$ hydrocarbyl. $R^{20}$ is typically unsubstituted $C_{8-30}$ alkyl or unsubstituted $C_{8-30}$ alkenyl. For instance, $R^{20}$ may be unsubstituted $C_{5-20}$ alkyl or unsubstituted $C_{8-20}$ alkenyl. n is typically from 5 to 10. Octaethylene glycol monododecyl ether and pentaethylene glycol monododecyl ether are examples of such non-ionic surfactant compounds.

The alkylphenol ethoxylates are typically selected from nonoxynols (polyethylene glycol nonyl phenyl ether) and Triton X-100 (polyethylene glycol p-(1,1,3,3-tetramethylbutyl)-phenyl ether). An example of a nonoxynol (a polyethylene glycol nonyl phenyl ether) is nonoxynol-9, which has the IUPAC name 2-[2-[2-[2-[2-[2-[2-[2-[2-(4-Nonylphenoxy)ethoxy]ethoxy]ethoxy]ethoxy]ethoxy]ethoxy]ethoxy]ethanol.

The ethoxylated amines and fatty acid amides, may for instance be selected from polyethoxylated tallow amine, cocamide monoethanolamine (which itself comprises compounds of formula $CH_3(CH_2)_nC(=O)NH(CH_2CH_2OH)$, where n typically ranges from 8 to 18, including lauramide monoethanolamine), and cocamide diethanolamine (which itself comprises compounds of formula $CH_3(CH_2)_nC(=O)N(CH_2CH_2OH)_2$, where n typically ranges from 8 to 18, including lauramide diethanolamine).

Poloxamers are nonionic triblock copolymers composed of a central hydrophobic chain of polyoxypropylene (poly(propylene oxide)) flanked by two hydrophilic chains of polyoxyethylene (poly(ethylene oxide)) and may for instance be of the formula $HO[CH_2CH_2O]_a[CH(CH_3)CH_2O]_b[CH_2CH_2O]_cH$ wherein a is an integer of from 2 to 130, b is an integer of 15 to 67 and c is an integer of from 2 to 130.

The alkyl polyglycosides may for instance be alkyl polyglucosides. The alkyl polyglucosides may for instance be alkyl polyglucosides of the following formula wherein m is from 1 to 5, and more typically 1 or 2, and wherein n is from 5 to 17, more typically from 7 to 13:

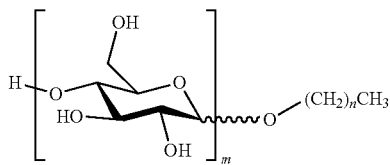

The alkyl glycosides and alkyl thioglycosides may for instance be alkyl glucosides or alkyl thioglucosides or alkyl maltosides. The alkyl glucosides may for instance be unsubstituted $C_{8-28}$ alkyl glucosides, and more typically unsubstituted $C_{8-20}$ alkyl glucosides, for instance unsubstituted $C_{8-12}$ alkyl glucosides. They may for instance be selected from octyl glucoside, decyl glucoside and lauryl glucoside. Alkyl thioglucosides, for instance octyl thioglucoside, may alternatively for instance be employed.

The amine oxide non-ionic surfactants are typically surfactants of formula $(R^4)(R^5)(R^6)N^+O^-$ wherein $R^4$ is a $C_{5-28}$ hydrocarbyl group, $R^5$ is an unsubstituted or substituted $C_{1-4}$ alkyl group, and $R^6$ is an unsubstituted or substituted $C_{1-4}$ alkyl group. Usually $R^5$ and $R^6$ are unsubstituted $C_{1-4}$ alkyl groups. Thus, usually, $R^4$, $R^5$ and $R^6$ are all unsubstituted groups. $R^4$ may be an unsubstituted $C_{8-28}$ alkyl or $C_{8-28}$ alkenyl group. Usually, $R^4$ is an unsubstituted $C_{8-20}$ alkyl group, for instance an unsubstituted $C_{10-14}$ alkyl group, such as a lauryl group. $R^5$ and $R^6$ are typically independently selected from methyl or ethyl groups, and are more typically both methyl groups. The non-ionic surfactant may for instance be lauryldimethylamine oxide (LDAO).

Preferably, the non-ionic surfactant comprises a non-ionic surfactant, or a mixture of two or more non-ionic surfactants, selected from fatty acid esters of sorbitan, fatty acid esters of ethoxylated sorbitan (polysorbates), fatty acid esters of glycerol, and fatty acid esters of sucrose.

More preferably, the non-ionic surfactant comprises a non-ionic surfactant, or a mixture of two or more non-ionic surfactants, selected from fatty acid esters of sorbitan and fatty acid esters of ethoxylated sorbitan (i.e. polysorbates), e.g. of formula (X) as defined above.

Usually, the non-ionic surfactant comprises a non-ionic surfactant, or a mixture of two or more (e.g. two or three) non-ionic surfactants, selected from polysorbates. The polysorbates may be of formula (X) as defined above wherein the sum of w, x, y and z is 20; $X^1$ and $X^2$ are both H. $R^1$ in formula (X) may for instance be unsubstituted $C_{8-20}$ alkyl or unsubstituted $C_{8-20}$ alkenyl.

Often, the non-ionic surfactant comprises a non-ionic surfactant, or a mixture of two or more (e.g. two or three) non-ionic surfactants, selected from polyoxyethylene (20) sorbitan monolaurate ("Tween 20"), polyoxyethylene (20) sorbitan monopalmitate ("Tween 40"), polyoxyethylene (20) sorbitan monostearate ("Tween 60"), and polyoxyethylene (20) sorbitan monooleate ("Tween 80"). Preferably, however, the non-ionic surfactant comprises, or consists of Tween 20, i.e. polyoxyethylene (20) sorbitan monolaurate.

Despite the fact that the tracer compounds employed in the present invention are retained in the fuel oil hydrocarbon phase even when extensively and vigorously water-washed, or when exposed to seawater, they can easily be extracted from the hydrocarbons for analysis using a non-ionic surfactant such as those described above.

The non-ionic surfactant may be employed at any suitable concentration in the aqueous extractant composition. For instance, the concentration of the non-ionic surfactant in the aqueous extractant composition may be greater than 1 vol. %, for example at least 2 vol. %, or at least 5 vol. %. However, it is a finding of the invention that non-ionic surfactant performed particularly well at concentrations of at least 10 vol. %, and in particular at concentrations of at least 15 vol. %, or for instance at concentrations of at least 20 vol. %, in the aqueous extractant composition.

Typically, therefore the concentration of the non-ionic surfactant in the aqueous extractant composition is at least 10 vol. %, for instance from 10 vol. % to 30 vol. %. The concentration of the non-ionic surfactant in the aqueous extractant composition may for instance be at least 15 vol. %, for instance from 15 vol. % to 35 vol. %, or for example from 15 vol. % to 25 vol. %. The concentration of the non-ionic surfactant in the aqueous extractant composition may for example be at least 18 vol. %, for instance from 18 vol. % to 38 vol. %, or for example from 18 vol. % to 28 vol. %. The non-ionic surfactant may as further defined above, for instance it may be a polysorbate or a mixture of polysorbates, and it may for instance comprise, or be, Tween 20.

Accordingly, the surfactant in the aqueous extractant composition may be Tween 20 and the concentration of the Tween 20 in the aqueous extractant composition may be at least 10 vol. %, for instance from 10 vol. % to 30 vol. %. The concentration of the Tween 20 in the aqueous extractant composition may for instance be at least 15 vol. %, for instance from 15 vol. % to 35 vol. %, or for example from 15 vol. % to 25 vol. %. The concentration of the Tween 20 in the aqueous extractant composition may for example be at least 18 vol. %, for instance from 18 vol. % to 38 vol. %, or for example from 18 vol. % to 28 vol. %. It is a finding of the invention that Tween 20 performed particularly well at these concentrations, in terms of extracting the tracer compounds employed in the present invention from fuel oil hydrocarbons. Step (iv), in the above defined methods comprises: analysing the identifiable oligonucleotide of the tracer compound to determine the identity of the oligonucleotide.

The identity of the oligonucleotide of the tracer compound can readily be determined by (a) amplifying the oligonucleotide; and (b) sequencing the amplified oligonucleotide.

The oligonucleotide may be amplified by performing PCR (the polymerase chain reaction) on the tracer compound. Accordingly, step (a) may comprise performing PCR on the tracer compound. PCR and sequencing are both very well known techniques. The PCR may for instance be qPCR (quantitative polymerase chain reaction), which is also well known.

Often, step (iv) of analysing the identifiable oligonucleotide of the tracer compound to determine the identity of the oligonucleotide comprises:

(a) amplifying the oligonucleotide in the presence of an intercalating reporter dye to determine that an oligonucleotide is present;

(b) optionally further amplifying the oligonucleotide; and (c) sequencing the amplified oligonucleotide and thereby determining the identity of the oligonucleotide.

The amplifying in steps (a) and (b) is typically achieved by performing PCR, for instance qPCR. The sequencing in step (c) may be by any suitable method. Methods for sequencing oligonucleotides are well known in the art.

Step (v) in the above-defined methods of the invention comprises using the identity of the oligonucleotide to identify information about the apolar medium. Step (v) may for instance comprises identifying the apolar medium as:

having been on board the watercraft from which the apolar medium was discharged into the water;

having been on board the watercraft from which the apolar medium was discharged into the water during the particular voyage on which the apolar medium was discharged; and/or having been present in a particular area, tank, container or bunker within the watercraft from which the apolar medium was discharged into the water during the particular voyage on which the apolar medium was discharged.

Uses

The invention further provides the use of a tracer compound for labelling an apolar medium, to enable identification of information about the apolar medium following discharge of the apolar medium from a watercraft into water, wherein the tracer compound comprises a hydrophobic group and an identifiable oligonucleotide. The discharge from the watercraft is typically an unlawful discharge of the apolar medium into water, for instance into the sea. As discussed hereinbefore, the tracer compound may for instance be used to label the apolar medium, to enable identification of the apolar medium as having been: on board said watercraft; on board said watercraft during a particular voyage; present in a particular area, tank, container or bunker within said watercraft; or present in a particular area, tank, container or bunker within said watercraft during a particular voyage. Therefore, said identifiable oligonucleotide typically comprises a sequence of nucleotides which identifies the apolar medium as having been: on board said watercraft; on board said watercraft during a particular voyage; present in a particular area, tank, container or bunker within said watercraft; or present in a particular area, tank, container or bunker within said watercraft during a particular voyage. The particular area, tank, container or bunker may be as further define hereinbefore for the methods of the invention. In this use of the invention, the tracer compound, apolar medium, and watercraft may be as further defined anywhere herein, and the use itself may be further defined in terms of any of the features of the methods of the invention defined herein.

The invention also provides the use of a tracer compound to identify information about an apolar medium following discharge of the apolar medium labelled with the tracer compound from a watercraft into water, wherein the tracer compound comprises a hydrophobic group and an identifiable oligonucleotide. The discharge from the watercraft is typically an unlawful discharge of the apolar medium into water, for instance into the sea. The tracer compound may be used to identify the apolar medium as having been: on board said watercraft; on board said watercraft during a particular voyage; present in a particular area, tank, container or bunker within said watercraft; or present in a particular area, tank, container or bunker within said watercraft during a particular voyage. The identifiable oligonucleotide typically therefore comprises a sequence of nucleotides which identifies the apolar medium as having been: on board said watercraft; on board said watercraft during a particular voyage; present in a particular area, tank, container or bunker within said watercraft; or present in a particular area, tank, container or bunker within said watercraft during a particular voyage. The particular area, tank, container or bunker may be as further define hereinbefore for the methods of the invention.

The invention will be further described in the Examples which follow.

EXAMPLES

Example 1

Introduction

Short chain length (ca. 80 bases in length) single stranded DNA molecules (oligonucleotides) can be readily produced by conventional DNA synthesis methodologies. The sequence of the bases within the oligonucleotide can be varied so that an almost unlimited number of unique oligonucleotide molecules can be generated.

The sequence of bases in the oligonucleotides can be also be varied to allow the identification and quantification of the oligonucleotide through quantitative polymerase chain reaction or variants of next generation sequencing technology.

The tagging and tracing of hydrocarbons requires that oligonucleotide tracer molecules can be readily dispersed in hydrocarbons, are resistant to leaching from the hydrocarbons if the latter is exposed to aqueous environments but can be recovered from the hydrocarbon to allow quantification and sequence detection.

Initial laboratory experiments showed that unmodified single stranded oligonucleotides could be dispersed into and recovered from hydrocarbons but their resistance to water leaching was problematic. Consequently, there was a need to design a system that still allowed the dispersion into and recovery of oligonucleotides from hydrocarbons but increased their resistance to aqueous leaching.

Experimental Approach

The approach adopted was to examine the effect of modifying the 5' end of the oligonucleotides with a hydrophobic moiety. The oligonucleotide used for these experiments has the base sequence of SEQ ID NO: 1, and was given the code name Zea02. The oligo was designed to be detected by quantitative polymerase chain reaction. The forward and reverse primer sequences, and the minor groove binder (MGB) probe sequence, that were employed in the quantitative polymerase chain reaction are SEQ ID NOs: 2, 3 and 4 respectively.

The structures of the hydrophobic modifications of Zea02 are shown in FIGS. 1 and 2. In each of the structures shown in FIGS. 1 and 2, the structure:

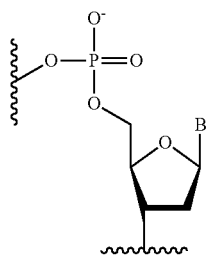

represents the nucleotide at the 5' end of the Zea-02 oligonucleotide, wherein B is the nitrogenous base of that nucleotide, cytosine (C). "DNA" represents the other nucleotides of the Zea-02 oligonucleotide.

These seven modified oligonucleotides along with an unmodified oligonucleotide were purchased from ATDBio (www.atdbio.com). The oligos were received as lyophilised (freeze dried) powders. The first experiment was to determine whether the hydrophobic modifications allowed the amplification of the oligonucleotides in a conventional qPCR reaction. The conventional qPCR reaction followed standard protocols which can be found in a series of web pages put together by Thermo Fisher, who now own Applied Biosystems (the original developers of the qPCR procedure). These protocols can be found at the following web address: http://www.thermofisher.com/uk/en/home/life-science/per/real-time-per/real-time-per-assays.html The lyophilised oligos were reconstituted with 1 ml of molecular grade water, serially diluted and then analysed using qPCR. The recovery of the modified oligos during reconstitution was calculated by comparing the amount recovered with those fro the unmodified control. The amplification efficiency for each modified was determined using the slope of each standards curve, which was generated from the results obtained from the amplification of the serial dilutions.

This preliminary screening experiment showed that the modified oligos all amplified with acceptable amplification efficiencies (85%). The amplification efficiencies and reconstitution recoveries of the modified oligos are shown in Table 1.

TABLE 1

Amplification efficiency and reconstitution recoveries for modified oligos following water addition

| Oligo modification | Amplification efficiency (%) | Reconstitution recovery (%) |
| --- | --- | --- |
| None | 98 | 97 |
| C12-amino | 91 | 75 |
| Stearyl | 97 | 91 |
| Palmitate | 94 | 65 |
| Cholesterol-TEG | 98 | 82 |
| Cholesterol | 100 | 6 |
| Tocopherol | 101 | 100 |
| Octyl-Tocopherol | 93 | 81 |

An aqueous solution of each oligo at a nominal concentration of 1e12 copies per ml was prepared. A series of 0.1 ml aliquots of each oligo placed in 3 ml Eppendorf tubes, which were dried under vacuum. One tube of each oligo had either 0.1 ml water, ethanol, xylene, tetrahydrofuran (THF) or octane added to it. The tubes were vigorously vortexed and then spun. 90 μl of the solution in each tube was taken and added to a separate Eppendorf tube. The solutions were then removed thorough vacuum drying and 100 μl of molecular grade water added to each tube, which were then vigorously vortexed. The copy number present in each tube was then determined through qPCR analysis.

The results obtained showed excellent recoveries for the palmitate and C12-amino oligos, when water and THF were used as the initial solvents. Palmitate and C12-amino were chosen for the further work described in this Example.

40 μl aliquots of oligo solutions of nominal concentrations of 1e12 copies per ml were vacuum dried and then resuspended in 400 ul of THF, which was then added to 3.6 ml of octane to give a final volume of 4 ml. 1 ml aliquots of this solution was then added to 9 ml of octane, marine diesel, intermediate fuel oil and heavy fuel oil.

1 ml of water was then added to each 10 ml aliquot of each hydrocarbon and the samples vortexed vigorously. The water phase was then analysed to determine the concentration of each oligo. The results demonstrated that the two oligos (Zea-02-Palmitate and Zea-02-C12-Amino) were washed out of the octane by the water washing. However, recoveries of the oligos from the marine diesel, intermediate fuel and heavy fuel were low with the palmitate oligo showing recoveries into the water phase of less than 0.5%.

Similar results were obtained when the water to hydrocarbon wash ratio was increased from 1:10 to 10:1. The results are shown in Table 2.

TABLE 2

Recoveries from hydrocarbons following water washing (9 parts water to 1 part hydrocarbon by volume)

| | % Recoveries into water phase | |
| --- | --- | --- |
| Hydrocarbon | C12-amino | Palmitate |
| Marine diesel | 2 | 49 |
| Intermediate fuel oil | <0.5 | 37 |
| Heavy fuel oil | <0.5 | 5 |

These initial experiments demonstrated that the alkyl hydrophobic modifications tested (C12-amino and palmitate) showed high propensity for remaining with fuel oil hydrocarbons (marine diesel, intermediate fuel oil and heavy fuel) even when extensively and vigorously water washed under laboratory conditions, with the C12-amino oligo showing recoveries into the water phase of less than 0.5%.

The oligos associated with the fuel hydrocarbons following the water washing were recovered using a specific aqueous buffer formulation (a "recovery buffer") which is commercially available from a company called TraceTag (see: www.tracetag.com). The recovery buffer contained surfactants adapted to aid extraction of the hydrocarbon fuel that needed to be tested. The recovery buffer did not effect the efficiency of amplification during identification and quantification of the oligos by qPCR. Example 2 below concerns, in part, the development of a recovery buffer which provided improved extraction performance compared to the recovery buffer employed in this Example. A surprisingly high proportion of the oligos in the hydrocarbon fraction could be extracted using the improved extraction buffer of Example 2.

Example 2

Development of Tween Based Extraction Buffer

Initial work had shown that the hydrophobic modification resulted in the oligonucleotide tracers having significantly increased propensity for remaining with the oil phase when shaken with water. However, the modified oligos have to be efficiently extracted from the oil to allow PCR amplification and subsequent sequencing.

Simple water based extraction was not sufficient.

It was postulated that non-ionic surfactants, also known as non-ionic detergents, may promote the migration of the modified oligonucleotides from the oil phase into the aqueous phase. Work focussed on use of the non-ionic detergent Tween 20. Other non-ionic detergents are available, any of which might suitably be employed as alternatives to Tween 20, although others were not trialled.

Tween 20 is a registered trade mark for the non ionic detergent polysorbate 20. Its correct (IUPAC) name is polyoxyethylene (20) sorbitan monolaurate. Tween 20, a viscous liquid in neat form, is produced by the ethoxylation of sorbitan before the addition of lauric acid; the ethoxylation process provides the molecule with 20 repeat units of polyethylene glycol and in practice these are distributed across 4 different chains leading to a commercial product containing a range of chemical species. Thus, Tween 20 has the molecular formula $C_{58}H_{114}O_{26}$ and its structure may be represented as follows:

concentration of $1.1 \times 10^{11}$/ml of taggant molecules. 5 μl of the tagged LPO was added to 380 ul of either the 20 vol. % or 2 vol. % Tween 20 solutions or to the same volume of distilled water in 1.5 ml Eppendorf tubes. The tubes were vigorously vortexed and allowed to settle for 10 minutes. The Tween 20 phase or the water phase was then serially diluted in distilled water and the copy number of the recovered oligonucleotide in the 1:100 dilution determined. This dilution is required to overcome inhibition from co-extracted in PCR inhibitors. The results obtained are presented in the Table 3 below and are shown as the determined % recovery compared to the theoretical extraction:

TABLE 3

Recoveries of 5' stearyl from light paraffin oil by extraction using Tween 20 or water as a control.

| Extractant | Extractant Dilution | Recovery as a % of Theoretical 100% Recovery |
| --- | --- | --- |
| Water | 1:100 | 0.9% |
| Tween 20 2% | 1:100 | 4.6% |
| Tween 20 20% | 1:100 | 10.5% |

Thin Film Stability Studies

The development work had focussed on examining the stability of the modified oligos in oils under static batch conditions followed by vigorous attempts to extract the modified oligonucleotides into the water.

There was a need to determine whether the modified oligonucleotides would remain with oil when the oil was layered on top of seawater in particular. This was known as the thin film experiments.

1 ml a light paraffin oil (LPO) and 1 ml of a light crude oil (LCO) were tagged with a modified oligo (5' stearyl, i.e. Zea02-Stearyl, whose structure is described in Example 1 and FIG. 1) to give a final concentration of $2.1 \times 10^{12}$/ml of taggant molecules. The 1 ml of LPO was then layered on top of 1.5 litres of water containing 35 g of sodium chloride per litre. The water was contained in an aluminium foil tray of dimensions (50 cm length×30 cm wide×5 cms deep). The 1 ml of LCO was layered on top of a separate 1.5 litres of water containing 35 g of sodium chloride per litre of water in a separate aluminium tray. Both oils spread out across the top of the water and formed a very thin film. The trays were not shaken or stirred and the experiment was carried out under static conditions.

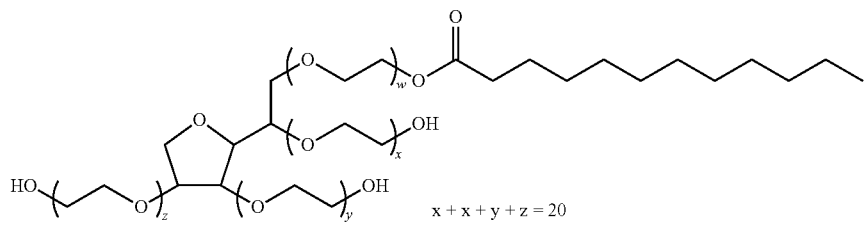

Tween 20 was purchased from Fisher Scientific.

Tween 20 was made up as 20% and 2% (v/v) solutions in distilled water.

20 ml a light paraffin oil (LPO) was tagged with a modified oligo (5' stearyl, i.e. Zea02-Stearyl, whose structure is described in Example 1 and FIG. 1) to give a final 5 μl of the tagged LPO or LCO recovered from the surface of the water and added to separate 380 μl of 20% Tween 20 extractant in 1.5 ml Eppendorf tubes. The tubes were vigorously vortexed and allowed to settle for 10 minutes. The Tween 20 phase was then serially diluted in distilled water and the copy number of the recovered oligonucleotide in the 1:100 dilution determined. This dilution is required to overcome inhibition from co-extracted in PCR inhibitors.

The results obtained are presented in Table 4 below and are shown as the concentration of oligonucleotide remaining in the oil expressed as a % of the original concentration.

TABLE 4

Retention of 5' stearyl in oil layered on salt water

| Oil | % Remaining in Oil on Day | |
|---|---|---|
| | 3 | 6 |
| Light paraffin oil | 76 | 65 |
| Light crude oil | 75 | 73 |

SEQUENCE LISTINGS

SEQ ID NO: 1 (Zea02 single-stranded oligonucleotide)
CCCCATCAGCACAAAGCTACAAAGGCCTAATGGGCGCGATTAAGGTCAAGGCTCAGTCCA SEQ ID NO: 2 (Forward primer)
CCCCATCAGCACAAAGCTACA SEQ ID NO: 3 (Reverse primer)
TGGACTGAGCCTTGACCTTAATC SEQ ID NO: 4 (minor groove binder (MGB) probe)
AGGCCTAATGGGCG

The invention claimed is:
1. A process for retrieving a tracer compound from a composition which comprises an apolar medium, the tracer compound and water, which tracer compound comprises a hydrophobic group and an identifiable oligonucleotide, wherein the hydrophobic group is covalently bonded to the oligonucleotide, which process comprises:
(a) separating at least some of the apolar medium from water in the composition; and
(b) extracting the tracer compound from the separated apolar medium, wherein extracting the tracer compound from the separated apolar medium comprises contacting the separated labelled apolar medium with an aqueous extractant composition which comprises water and a non-ionic surfactant.

2. A process according to claim 1, wherein the water comprises seawater.

3. A process according to claim 1, wherein the non-ionic surfactant comprises a non-ionic surfactant, or a mixture of two or more non-ionic surfactants, selected from: fatty acid esters of polyhydroxy compounds, fatty alcohol ethoxylates, alkylphenol ethoxylates, ethoxylated amines, fatty acid amides, poloxamers, alkyl polyglycosides (APGs), alkyl glycosides, alkyl thioglycosides and amine oxide non-ionic surfactants.

4. A process according to claim 1, wherein the non-ionic surfactant comprises a non-ionic surfactant, or a mixture of two or more non-ionic surfactants, of formula (X)

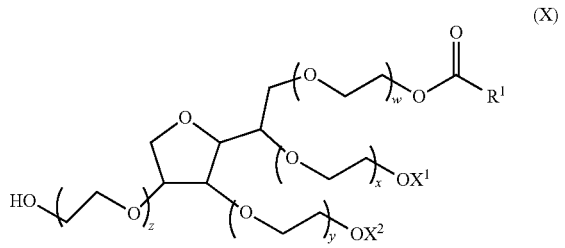

(X)

wherein
w is 0 or an integer of from 1 to 20;
x is 0 or an integer of from 1 to 20;
y is 0 or an integer of from 1 to 20;
z is 0 or an integer of from 1 to 20;
$R^1$ is $C_{8-30}$ hydrocarbyl;
$X^1$ is H or $C(O)R^{11}$, wherein $R^{11}$ is $C_{8-30}$ hydrocarbyl; and
$X^2$ is H or $C(O)R^{12}$, wherein $R^{12}$ is $C_{8-30}$ hydrocarbyl.

5. A process according to claim 1, wherein the non-ionic surfactant comprises polyoxyethylene (20) sorbitan monolaurate (Tween 20) and the concentration of the non-ionic surfactant in the aqueous extractant composition is at least 10 vol. %.

6. A process according to claim 1, wherein the tracer compound is a compound of formula (I)

(I)

wherein
Tag is said oligonucleotide;
R is said hydrophobic group, wherein R is covalently bonded directly to an oxygen atom of a phosphate group of a nucleotide at the 5' end of Tag, or R is covalently bonded directly to an oxygen atom of a phosphate group at the 3' end of Tag, wherein another oxygen atom of the phosphate group at the 3' end of Tag is covalently bonded directly to the 3' ring carbon of the nucleotide at the 3' end of Tag; and
said group R:
(a) is an unsubstituted or substituted $C_{4-200}$ hydrocarbyl group; or
(b) is a group of formula (II)

(II)

wherein
$R^{HC}$ is an unsubstituted or substituted hydrocarbyl group; and
L is bonded to Tag and is a linker group, wherein L is unsubstituted or substituted $C_{1-200}$ hydrocarbylene, unsubstituted or substituted $C_{1-200}$ alkylene, unsubstituted or substituted $C_{4-30}$ cycloalkylene, unsubstituted or substituted $C_{2-200}$ alkenylene, unsubstituted or substituted $C_{2-200}$ alkynylene, unsubstituted or substituted $C_{6-16}$ arylene or heteroarylene, —O—, —S—, —NR'—, —C(O)—NR'—, —O—C(O)—NR'—, or [—O-alk-]$_n$, or L is two or more of these groups, which may be the same or different, bonded to one another, wherein alk is $C_{2-4}$ alkylene, n is from 2 to 200, and R' is H, unsubstituted $C_{1-4}$ alkyl or unsubstituted phenyl; or
(c) comprises a hydrophobic polymer which is a hydrocarbon polymer.

7. A process according to claim 6, wherein:
(A) R is said unsubstituted or substituted $C_{4-200}$ hydrocarbyl group, wherein: R is an unsubstituted $C_{10-50}$ alkyl group or an amino-substituted $C_{10-50}$ alkyl group, or R is a substituted $C_{4-200}$ hydrocarbyl group which is a $C_{4-200}$ perfluorohydrocarbyl group;
or
(B) R is said group of formula (II), wherein:
$R^{HC}$ is an unsubstituted $C_{6-50}$ alkyl group or a group of the following formula:

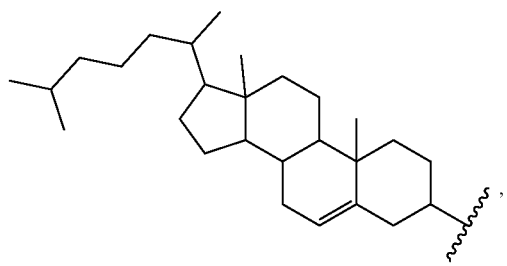 [SMILES: *C1CCC2(C)C(=CCC3C2CCC2(C)C(C(C)CCCC(C)C)CCC32)C1]

or $R^{HC}$ is a substituted hydrocarbyl group which is a $C_{4-200}$ perfluorohydrocarbyl group; and
L is a group of the formula:

wherein:
$L^1$ is bonded to Tag and is unsubstituted or substituted $C_{1-200}$ hydrocarbylene, unsubstituted or substituted $C_{6-16}$ arylene or heteroarylene, or [—O-alk-]$_n$, wherein alk is linear or branched unsubstituted $C_{2-4}$ alkylene and n is from 2 to 200;
$L^2$ is a single bond, unsubstituted or substituted $C_{1-200}$ hydrocarbylene, —O—, —N(R')—, —C(O)—, —C(O)—N(R')— or —O—C(O)—NR'—; and
$L^3$ is a single bond, —O—C(O)—NR'—, unsubstituted or substituted $C_{6-16}$ arylene or heteroarylene, wherein R' is H, unsubstituted $C_{1-4}$ alkyl or unsubstituted phenyl;

or (C) R comprises said hydrophobic polymer which is a hydrocarbon polymer, wherein the hydrocarbon polymer is a polyolefin or a polyolefin elastomer.

8. A process according to claim 6 wherein said group R:
(a) is an unsubstituted or substituted $C_4$-200 hydrocarbyl group; or
(b) is a group of formula (II)

$$R^{HC}\text{-L-} \qquad (II)$$

wherein
$R^{HC}$ is an unsubstituted or substituted hydrocarbyl group; and
L is bonded to Tag and is a linker group, wherein L is unsubstituted or substituted $C_{1-200}$ hydrocarbylene, unsubstituted or substituted $C_{1-200}$ alkylene, unsubstituted or substituted $C_{4-30}$ cycloalkylene, unsubstituted or substituted $C_{2-200}$ alkenylene, unsubstituted or substituted $C_{2-200}$ alkynylene, unsubstituted or substituted $C_{6-16}$ arylene or heteroarylene, —O—, —S—, —NR'—, —C(O)—NR'—, —O—C(O)—NR'—, or [—O-alk-]$_n$, or L is two or more of these groups, which may be the same or different, bonded to one another, wherein alk is $C_{2-4}$ alkylene, n is from 2 to 200, and R' is H, unsubstituted $C_{1-4}$ alkyl or unsubstituted phenyl.

9. A process according to claim 6 wherein:
(A) R is an unsubstituted $C_{10-50}$ alkyl group or an amino-substituted $C_{10-50}$ alkyl group;
or
(B) R is said group of formula (II), wherein:
$R^{HC}$ is an unsubstituted $C_{6-50}$ alkyl group or a group of the following formula:

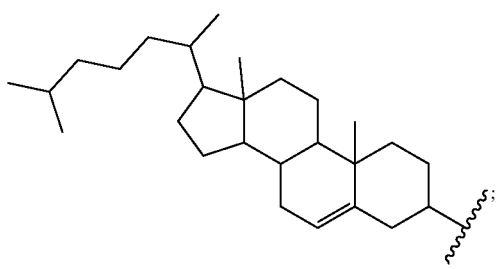 [SMILES: *C1CCC2(C)C(=CCC3C2CCC2(C)C(C(C)CCCC(C)C)CCC32)C1]

and
L is a group of the formula:

-L$^3$-L$^2$-L$^1$- wherein:
L$^1$ is bonded to Tag and is unsubstituted or substituted $C_{1-200}$ hydrocarbylene, unsubstituted or substituted $C_{6-16}$ arylene or heteroarylene, or [—O-alk-]$_n$, wherein alk is linear or branched unsubstituted $C_{2-4}$ alkylene and n is from 2 to 200;
L$^2$ is a single bond, unsubstituted or substituted $C_1$-200 hydrocarbylene, —O—, —N(R')—, —C(O)—, —C(O)—N(R')— or —O—C(O)—NR'—; and
L$^3$ is a single bond, —O—C(O)—NR'—, unsubstituted or substituted $C_{6-16}$ arylene or heteroarylene,
wherein R' is H, unsubstituted $C_{1-4}$ alkyl or unsubstituted phenyl.

10. A process according to claim 6 wherein the hydrophobic group R is a first hydrophobic group and the tracer compound further comprises a second hydrophobic group, $R^{II}$, wherein the second hydrophobic group is the same as or different from the first hydrophobic group, wherein the tracer compound is a compound of formula (V)

$$R\text{-Tag-}R^{II} \qquad (V)$$

wherein
R is the first hydrophobic group and is as defined in claim 6;
$R^{II}$ is the second hydrophobic group; and
Tag is the oligonucleotide,
wherein:
one of R and $R^{II}$ is covalently bonded directly to an oxygen atom of the phosphate group of the nucleotide at the 5' end of Tag; and
the other one of R and $R^{II}$ is covalently bonded directly to an oxygen atom of a phosphate group at the 3' end of Tag, wherein another oxygen atom of the phosphate group at the 3' end of Tag is covalently bonded directly to the 3' ring carbon of the nucleotide at the 3' end of Tag.

11. A process according to claim 6 wherein the water comprises seawater.

12. A process according to claim 6 wherein the non-ionic surfactant comprises a non-ionic surfactant, or a mixture of two or more non-ionic surfactants, selected from: fatty acid esters of polyhydroxy compounds, fatty alcohol ethoxylates, alkylphenol ethoxylates, ethoxylated amines, fatty acid amides, poloxamers, alkyl polyglycosides (APGs), alkyl glycosides, alkyl thioglycosides and amine oxide non-ionic surfactants.

13. A process according to claim 6 wherein the non-ionic surfactant comprises a non-ionic surfactant, or a mixture of two or more non-ionic surfactants, of formula (X)

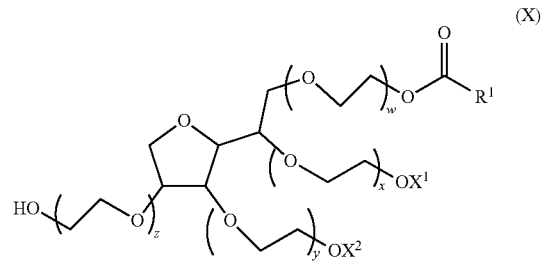

wherein
w is 0 or an integer of from 1 to 20;
x is 0 or an integer of from 1 to 20;
y is 0 or an integer of from 1 to 20;
z is 0 or an integer of from 1 to 20;
$R^1$ is $C_{8-30}$ hydrocarbyl;
$X^1$ is H or $C(O)R^{11}$, wherein $R^{11}$ is $C_{8-30}$ hydrocarbyl; and
$X^2$ is H or $C(O)R^{12}$, wherein $R^{12}$ is $C_{8-30}$ hydrocarbyl.

14. A process according to claim 6 wherein the non-ionic surfactant comprises polyoxyethylene (20) sorbitan monolaurate (Tween 20), wherein the concentration of the non-ionic surfactant in the aqueous extractant composition is at least 10 vol. %.

15. A process according to claim 6 wherein:
the non-ionic surfactant comprises a non-ionic surfactant, or a mixture of two or more non-ionic surfactants, selected from: fatty acid esters of polyhydroxy compounds, fatty alcohol ethoxylates, alkylphenol ethoxylates, ethoxylated amines, fatty acid amides, poloxamers, alkyl polyglycosides (APGs), alkyl glycosides, alkyl thioglycosides and amine oxide non-ionic surfactants; and said group R:
(a) is an unsubstituted or substituted $C_4$-200 hydrocarbyl group; or
(b) is a group of formula (II)

  (II)

wherein
$R^{HC}$ is an unsubstituted or substituted hydrocarbyl group; and
L is bonded to Tag and is a linker group, wherein L is unsubstituted or substituted $C_{1-200}$ hydrocarbylene, unsubstituted or substituted $C_{1-200}$ alkylene, unsubstituted or substituted $C_{4-30}$ cycloalkylene, unsubstituted or substituted $C_{2-200}$ alkenylene, unsubstituted or substituted $C_2$-200 alkynylene, unsubstituted or substituted $C_{6-16}$ arylene or heteroarylene, —O—, —S—, —NR'—, —C(O)—NR'—, —O—C(O)—NR'—, or [—O-alk-]$_n$, or L is two or more of these groups, which may be the same or different, bonded to one another, wherein alk is $C_{2-4}$ alkylene, n is from 2 to 200, and R' is H, unsubstituted $C_{1-4}$ alkyl or unsubstituted phenyl.

16. A process according to claim 6 wherein:
the non-ionic surfactant comprises a non-ionic surfactant, or a mixture of two or more non-ionic surfactants, of formula (X)

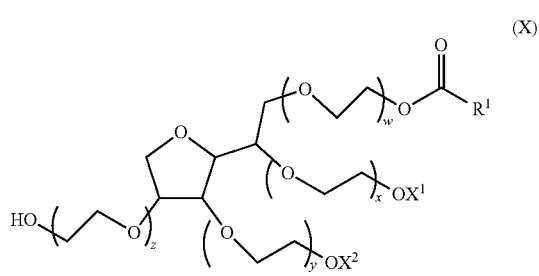

wherein
w is 0 or an integer of from 1 to 20;
x is 0 or an integer of from 1 to 20;
y is 0 or an integer of from 1 to 20;
z is 0 or an integer of from 1 to 20;
$R^1$ is $C_{8-30}$ hydrocarbyl;
$X^1$ is H or C(O)$R^{11}$, wherein $R^{11}$ is $C_{8-30}$ hydrocarbyl; and
$X^2$ is H or C(O)$R^{12}$, wherein $R^{12}$ is $C_{8-30}$ hydrocarbyl,
and wherein said group R in the compound of formula (I) is:
(A) an unsubstituted $C_{10-50}$ alkyl group or an amino-substituted $C_{10-50}$ alkyl group; or
(B) said group of formula (II), wherein:
$R^{HC}$ is an unsubstituted $C_{6-50}$ alkyl group or a group of the following formula:

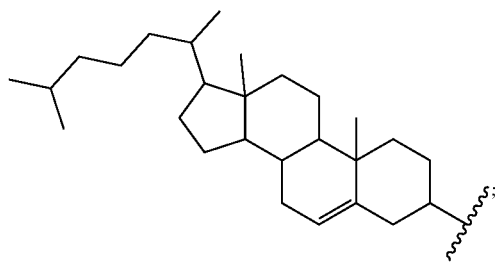 [SMILES: *C1CCC2(C)C(=CCC3C2CCC2(C)C(C(C)CCCC(C)C)CCC32)C1]

and
L is a group of the formula:

wherein:
$L^1$ is bonded to Tag and is unsubstituted or substituted $C_{1-200}$ hydrocarbylene, unsubstituted or substituted $C_{6-16}$ arylene or heteroarylene, or [—O-alk-]$_n$, wherein alk is linear or branched unsubstituted $C_{2-4}$ alkylene and n is from 2 to 200;
$L^2$ is a single bond, unsubstituted or substituted $C_{1-200}$ hydrocarbylene, —O—, —N(R')—, —C(O)—, —C(O)—N(R')— or —O—C(O)—NR'—; and
$L^3$ is a single bond, —O—C(O)—NR'—, unsubstituted or substituted $C_{6-16}$ arylene or heteroarylene, wherein R' is H, unsubstituted $C_{1-4}$ alkyl or unsubstituted phenyl.

17. A process according to claim 6 wherein:
the non-ionic surfactant comprises polyoxyethylene (20) sorbitan monolaurate (Tween 20), wherein the concentration of the non-ionic surfactant in the aqueous extractant composition is at least 10 vol. %; and
said group R in the compound of formula (I) is a group of any one of the following formulae:

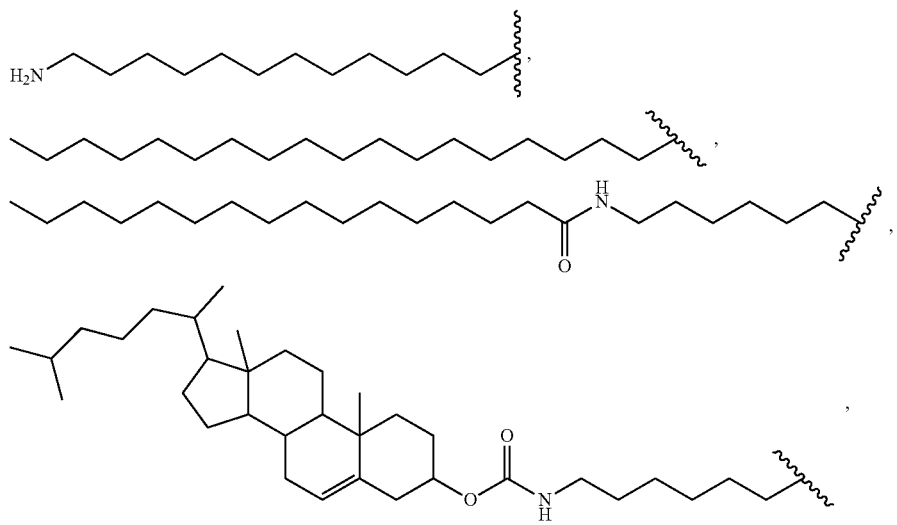

-continued
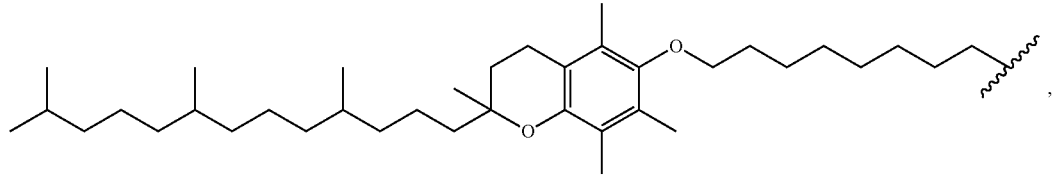
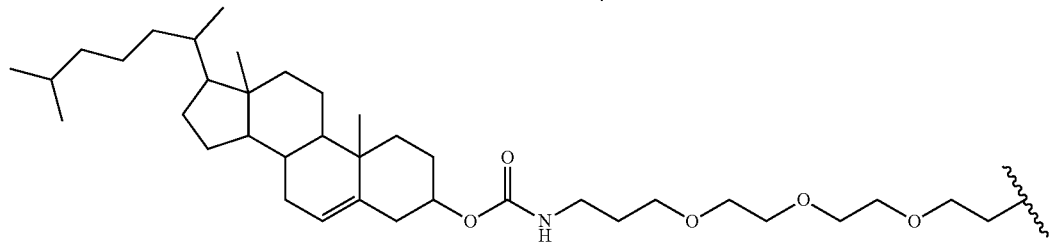
and 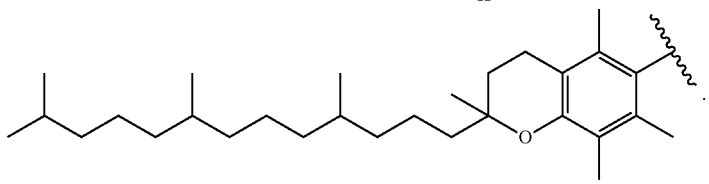
* * * * *

UNITED STATES PATENT AND TRADEMARK OFFICE
CERTIFICATE OF CORRECTION

PATENT NO. : 11,370,984 B2
APPLICATION NO. : 16/481798
DATED : June 28, 2022
INVENTOR(S) : Robert Sleat et al.

Page 1 of 1

It is certified that error appears in the above-identified patent and that said Letters Patent is hereby corrected as shown below:

In the Specification

Column 12, Line 24, [ [($C_{5-24}$)] ] should read as --($C_{8-24}$)--.
Column 16, Line 61, [ [$C_{is}$] ] should read as --$C_{18}$--.
Column 17, Line 54, [ [$C_{is-so}$] ] should read as --$C_{15-50}$--.
Column 19, Line 6, [ [$C_{is-so}$] ] should read as --$C_{15-50}$--.
Column 39, Line 66, [ [$C_{5-30}$] ] should read as --$C_{8-30}$--.
Column 40, Line 2, [ [$C_{is}$] ] should read as --$C_{15}$--.
Column 40, Line 9, [ [$R^1$] ] should read as --$R^{11}$--.
Column 40, Line 11, [ [$C_{is}$] ] should read as --$C_{15}$--.
Colum 40, Line 20, [ [$C_{is}$] ] should read as --$C_{15}$--.
Column 40, Line 35, [ [$C_{5-20}$] ] should read as --$C_{8-20}$--.
Column 40, Line 57, [ [$R^1$] ] should read as --$R^{11}$--.
Column 41, Line 3, [ [$C_{5-20}$] ] should read as --$C_{8-20}$--.
Column 41, Line 18, [ [$C_{5-20}$] ] should read as --$C_{8-20}$--.
Column 42, Line 5, [ [$C_{5-28}$] ] should read as --$C_{8-28}$--.
Column 44, Lines 61-62, [ [The sequence of bases in the oligonucleotides can be also be varied] ] should read as --The sequence of bases in the oligonucleotides can also be varied--.
Column 45, Lines 55-56 should read as --http://www.thermofisher.com/uk/en/home/life-science/pcr/real-time-pcr/real-time-pcr-assays.html--.
Column 47, the structure [ [x+x+y+z-20] ] should read as --w+x+y+z-20′--.

Signed and Sealed this
Sixteenth Day of August, 2022

Katherine Kelly Vidal
*Director of the United States Patent and Trademark Office*